(12) United States Patent
Priepke et al.

(10) Patent No.: US 7,005,437 B2
(45) Date of Patent: Feb. 28, 2006

(54) SUBSTITUTED ARYL AND HETEROARYL DERIVATIVES, THE PREPARATION THEREOF AND THE USE THEROF AS PHARMACEUTICAL COMPOSITIONS

(75) Inventors: Henning Priepke, Warthausen (DE); Uwe Ries, Biberach (DE); Herbert Nar, Ochsenhausen (DE); Wolfgang Wienen, Biberach/Rissegg (DE); Jean-Marie Stassen, Lubbeek (BE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 316 days.

(21) Appl. No.: 10/142,699

(22) Filed: May 10, 2002

(65) Prior Publication Data

US 2003/0045712 A1 Mar. 6, 2003

Related U.S. Application Data

(60) Provisional application No. 60/295,435, filed on Jun. 1, 2001.

(30) Foreign Application Priority Data

May 22, 2001 (DE) ................................ 101 24 867

(51) Int. Cl.
| | |
|---|---|
| A61K 31/445 | (2006.01) |
| A61K 31/44 | (2006.01) |
| A61K 31/40 | (2006.01) |
| C07D 301/00 | (2006.01) |
| C07D 211/68 | (2006.01) |

(52) U.S. Cl. ............... 514/318; 514/343; 514/326; 514/423; 549/539; 546/193; 546/279.1; 560/121; 564/163; 564/245

(58) Field of Classification Search ............... 546/223, 546/225, 226, 227, 229, 231, 232, 233, 279.1; 514/330, 423, 343; 549/953, 539; 564/163, 564/245

See application file for complete search history.

(56) References Cited

FOREIGN PATENT DOCUMENTS

| | | |
|---|---|---|
| WO | WO 97/30971 | 8/1997 |
| WO | WO 00/35859 | 6/2000 |
| WO | WO 00/71512 A1 | 11/2000 |
| WO | WO 01/10823 A1 | 2/2001 |

OTHER PUBLICATIONS

Hcaplus 129:275676, "Synthesis of cinnamaldehydes by oxidation of arylpropenes with 2,3-dichloro-5,6-dicyanoquinone", 1998, 52(9), pp. 1177-1182.*
R. Rai et al; Perspectives on Factor Xa Inhibition; Current Medicinal Chemistry 2001, vol. 8 pages 101-119; Bentham Science Publishers, Ltd.
Fevig, J.M. et al: "Preparation of meta-amidino-N,N-disunstituted anilines as potent inhibitors of coagulation factor Xa" Bioorganic & Medicinal Chemistry Letters, Oxford, GB, Bd. 8, Nr. 22, Nov. 17, 1998, Seiten 3143-3146, XP004143716 ISSN: 0960-894X.

* cited by examiner

*Primary Examiner*—James O. Wilson
*Assistant Examiner*—Binta M. Robinson
(74) *Attorney, Agent, or Firm*—Michael P. Morris; Mary-Ellen M. Devlin; Alan R. Stempel

(57) ABSTRACT

The present invention relates to new substituted aryl and heteroaryl derivatives of general formula

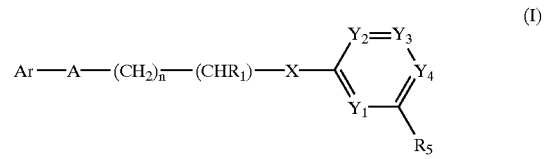

(I)

wherein
A, Ar, n, X, $Y_1$, $Y_2$, $Y_3$, $Y_4$, $R_1$ and $R_5$ are defined as in claim 1, the prodrugs, the tautomers, stereoisomers, mixtures thereof and the salts thereof, particularly the physiologically acceptable salts thereof with inorganic or organic acids or bases which have valuable properties. Thus, the compounds of the above general formula I wherein $R_5$ does not contain a cyano group have, in particular, an antithrombotic effect and a selective factor Xa-inhibiting effect with generally improved compatibility. The compounds of the above general formula I wherein $R_5$ contains a cyano group are valuable intermediate products for preparing the antithrombotic compounds of general formula I.

9 Claims, No Drawings

SUBSTITUTED ARYL AND HETEROARYL DERIVATIVES, THE PREPARATION THEREOF AND THE USE THEROF AS PHARMACEUTICAL COMPOSITIONS

Substituted aryl and heteroaryl derivatives with an antithrombotic effect are already known from WO 00/35859.

The present invention relates to new substituted aryl and heteroaryl derivatives of general formula (I)

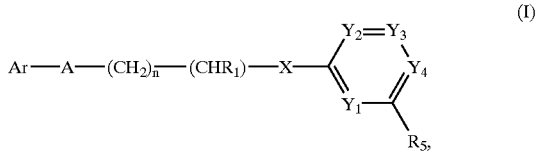

the prodrugs, the tautomers, the stereoisomers, the mixtures and the salts thereof, particularly the physiologically acceptable salts thereof with inorganic or organic acids or bases, which have valuable properties.

The compounds of the above general formula I wherein $R_5$ does not contain a cyano group, have valuable pharmacological properties, particularly an antithrombotic effect and a selective factor Xa-inhibiting effect, and the compounds of the above general formula I wherein $R_5$ contains a cyano group, constitute valuable intermediate products for preparing the compounds of general formula I wherein $R_5$ denotes an optionally substituted amidino group.

The present invention thus relates to new compounds of the above general formula I as well as the preparation thereof, the pharmaceutical compositions containing the pharmacologically effective compounds and the use thereof.

In the above general formula I

A denotes an ethynylene or an ethylene group, n denotes one of the numbers 0 or 1, $R_1$ denotes a hydrogen atom, a $C_{1-3}$-alkyl, carboxy-$C_{1-3}$-alkyl, phenyl, phenyl-$C_{1-3}$-alkyl, heteroaryl, heteroaryl-$C_{1-3}$-alkyl, N-$C_{1-3}$-alkylaminocarbonyl-$C_{1-3}$-alkyl, N,N-Di-($C_{1-3}$-alkyl)-aminocarbonyl-$C_{1-3}$-alkyl or $C_{4-7}$-cycloalkyleneimino-carbonyl-$C_{1-3}$-alkyl group, Ar denotes a phenyl or pyridyl group substituted by the groups $R_2$ to $R_4$, while $R_2$ denotes a $C_{1-6}$-alkyl or $C_{3-7}$-cycloalkyl-$C_{1-3}$-alkyl group, while the acyclic alkyl moieties thereof may be substituted in each case by a carboxy, amino, $C_{1-3}$-alkylamino, carboxy-$C_{1-3}$-alkylamino, di-($C_{1-3}$-alkyl)-amino, pyrrolidino, piperidino, hexamethyleneimino, N-(carboxy-$C_{1-3}$-alkyl)-$C_{1-3}$-alkylamino or $C_{3-7}$-cycloalkylamino group, a carboxy-$C_{1-5}$-alkyl group which is substituted in the alkyl moiety by a $C_{1-3}$-alkylamino, N,N-di-($C_{1-3}$-alkyl)-amino, pyrrolidino, piperidino or hexamethyleneimino group, a carboxy-$C_{1-5}$-alkyl group wherein the hydrogen atoms of a methylene group are replaced by a n-$C_{2-5}$-alkylene bridge, a phenyl or heteroaryl group which may additionally be substituted in each case by a fluorine, chlorine, bromine or iodine atom, by a trifluoromethyl, $C_{1-3}$-alkyl, carboxy-$C_{1-3}$-alkyl, $C_{1-3}$-alkoxy, $C_{1-3}$-alkylsulphonyl, aminosulphonyl, $C_{1-3}$-alkylaminosulphonyl or di-($C_{1-3}$-alkyl)-aminosulphonyl group, a $C_{1-5}$-alkylamino, carboxy-$C_{1-3}$-alkylamino, di-($C_{1-5}$-alkyl)-amino, N-(carboxy-$C_{1-3}$-alkyl)-$C_{1-5}$-alkylamino, $C_{3-7}$-cycloalkylamino or N-(carboxy-$C_{1-3}$-alkyl)-$C_{3-7}$-cycloalkylamino group, a $C_{3-7}$-cycloalkylcarbonylamino, N-($C_{1-3}$-alkyl)-$C_{1-5}$-alkylcarbonylamino or N-($C_{1-3}$-alkyl)-$C_{3-7}$-cycloalkylcarbonylamino group, while the abovementioned N-($C_{1-3}$-alkyl) moieties may additionally be substituted by a carboxy, carboxy-$C_{1-3}$-alkylaminocarbonyl or N-($C_{1-3}$-alkyl)-carboxy-$C_{1-3}$-alkylaminocarbonyl group or, with the exception of the α-carbon atom based on the nitrogen atom, may also be substituted by a hydroxy, carboxy-$C_{1-3}$-alkoxy, amino, carboxy-$C_{1-3}$-alkylamino or N-($C_{1-3}$-alkyl)-carboxy-$C_{1-3}$-alkylamino group, a 5- to 7-membered cycloalkyleneimino group, an amino, $C_{1-5}$-alkylamino or $C_{3-7}$-cycloalkylamino group which is substituted in each case at the amino-nitrogen atom by a $C_{1-5}$-alkylcarbonyl, carboxy-$C_{1-3}$-alkylcarbonyl or carboxy-$C_{1-3}$-alkylaminocarbonyl group, while additionally the alkyl moiety of the abovementioned $C_{1-5}$-alkylcarbonyl- and carboxy-$C_{1-3}$-alkylcarbonyl group may be substituted by an amino, hydroxy, carboxy-$C_{1-3}$-alkoxy, carboxy-$C_{1-3}$-alkylaminocarbonyl, carboxy-$C_{1-3}$-alkylamino, N-($C_{1-3}$-alkyl)-carboxy-$C_{1-3}$-alkylamino or amino-$C_{1-3}$-alkylcarbonylamino group, a carbonyl group which is substituted by a $C_{1-5}$-alkyl or $C_{3-7}$-cycloalkyl group optionally substituted by a carboxy group, by a phenyl group which may be substituted by a fluorine, chlorine, bromine or iodine atom, by a $C_{1-3}$-alkyl, carboxy-$C_{1-3}$-alkyl, $C_{1-3}$-alkoxy, carboxy, $C_{1-3}$-alkyl-sulphonyl, aminosulphonyl, $C_{1-3}$-alkylaminosulphonyl, di-($C_{1-3}$-alkyl)-amino-sulphonyl group, by an amino, $C_{1-5}$-alkylamino, $C_{2-5}$-alkenylamino, $C_{3-6}$-alkynylamino, carboxy-$C_{1-3}$-alkylamino or $C_{3-7}$-cycloalkylamino group which may additionally be substituted in each case at the amino-nitrogen atom by a $C_{1-5}$-alkyl, $C_{3-7}$-cycloalkyl, carboxy-$C_{1-3}$-alkyl, amino-$C_{1-4}$-alkyl, $C_{1-3}$-amino-$C_{1-4}$-alkyl, 2-[di-($C_{1-3}$-alkyl)-amino]-ethyl, 3-[di-($C_{1-3}$-alkyl)-amino]-propyl, phenyl, pyridyl, pyrrolidinyl, piperidinyl, 2,5-dihydro-1H-pyrrolyl or 1,2,5,6-tetrahydropyridinyl group, by a pyrrolyl, thienyl, imidazolyl, pyrazolyl, thiazolyl, pyridinyl, pyrimidinyl, pyrazinyl or pyridazinyl group, optionally substituted by one or two $C_{1-3}$-alkyl groups, and to which a phenyl ring may be fused in each case via two adjacent carbon atoms, or by a $C_{3-6}$-cycloalkyleneimino or $C_{3-6}$-cycloalkenyleneimino group optionally substituted by a $C_{1-3}$-alkyl, carboxy-$C_{1-3}$-alkyl, hydroxy, hydroxy-$C_{1-3}$-alkyl, amino, carboxy, carboxy-$C_{1-3}$-alkoxy-$C_{1-3}$-alkyl, carboxy-$C_{1-3}$-alkylamino-$C_{1-3}$-alkyl or carboxy-$C_{1-3}$-alkylaminocarbonyl-$C_{1-3}$-alkyl group, with the proviso that the hydroxy and the amino groups are not bound in the 2-position, $R_3$ denotes a hydrogen, fluorine, chlorine, bromine or iodine atom, a formyl or trifluoromethyl group, a $C_{1-3}$-alkoxy, amino, $C_{1-2}$-alkylamino, di-($C_{1-2}$-alkyl)-amino or $C_{1-2}$-alkanoylamino group, a $C_{1-4}$-alkyl, $C_{2-4}$-alkenyl, $C_{2-4}$-Alkynyl or $C_{3-4}$-cycloalkyl group optionally substituted by a hydroxy, $C_{1-3}$-alkoxy, carboxy, carboxy-$C_{1-3}$-alkoxy or carboxy-$C_{1-3}$-alkylaminocarbonyl group and $R_4$ denotes a hydrogen, fluorine, chlorine, bromine or iodine atom, a $C_{1-3}$-alkyl, trifluoromethyl or $C_{1-3}$-alkoxy group, X denotes an oxygen or sulphur atom, a methylene group optionally substituted by one or two $C_{1-3}$-alkyl groups, a carbonyl, sulphinyl, sulphonyl, imino or N-($C_{1-3}$-alkyl)-imino group, a N-(phenyl-$C_{1-3}$-alkyl)-imino or N-(pyridyl-$C_{1-3}$-alkyl)-imino group optionally substituted by a carboxy group, a N-($C_{1-3}$-alkyl)-carbonylimino, N-(carboxy-$C_{1-3}$-alkyl)-imino, $C_{1-3}$-alkylaminocarbonyl-$C_{1-3}$-alkylimino, di-($C_{1-3}$-alkyl)-aminocarbonyl or $C_{1-3}$-alkylimino group, $R_5$ denotes a cyano or $C_{1-2}$-alkyl-cyano group or an amidino group optionally substituted by a group which can be cleaved in vivo and $Y_1$ denotes the group $CR^w$,
$Y_2$ denotes the group $CR^x$,
$Y_3$ denotes the group $CR^y$ and
$Y_4$ denotes the group $CR^z$ or one or two of the groups $Y_1$ to $Y_4$ denotes a nitrogen atom and in each case the remainder of the groups $Y_1$ to $Y_4$ denote three or two of the groups $CR^w$ to $CR^z$, while $R^w$, $R^x$, $R^y$ and $R^z$ in each case denote a hydrogen atom or one or two of the groups $R^w$ to $R^z$ independently of one another in each case denote a fluorine, chlorine or bromine atom, a straight-chain $C_{1-3}$-alkyl group, a hydroxy, $C_{1-3}$-alkoxy, amino, $C_{1-3}$-alkylamino or di-($C_{1-3}$-alkyl)-amino group and the remainder of the groups $R^w$ to $R^z$ in each case represent a hydrogen atom, while $R_5$ and $R^z$ together may also represent a group of formula

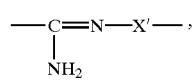

(II)

wherein

X' is bound in the 4 position relative to the group X in formula (I) and denotes a methylene or ethylene group, an oxygen atom, an imino or vinylene group, while particularly those compounds of general formula (I), wherein A denotes an ethynylene group, are of exceptional importance, while the hydrogen atoms in the methyl and methoxy groups mentioned in the definition of the above groups or in the methyl moieties contained in the groups of formula I defined hereinbefore may, unless otherwise stated, be wholly or partially replaced by fluorine atoms.

By the abovementioned heteroaryl group is meant a 5-membered heteroaromatic group, optionally substituted by one or two $C_{1-3}$-alkyl groups, which contains an imino group, optionally substituted by a $C_{1-3}$-alkyl group, an oxygen or sulphur atom or an imino group optionally substituted by a $C_{1-3}$-alkyl group, an oxygen or sulphur atom and one or two nitrogen atoms as well as the partially hydrogenated derivatives thereof, particularly the dihydro derivatives thereof, or a 6-membered heteroaromatic group which contains one, two or three nitrogen atoms, while additionally a phenyl ring may be fused to the abovementioned 5- and 6-membered heteroaromatic rings via two adjacent carbon atoms.

Moreover, the compounds according to the invention may be in the form of prodrugs. For example, the carboxy groups mentioned above in the definitions may be replaced by a tetrazolyl group or by a group which may be converted into a carboxy group in vivo, e.g. by a hydroxymethyl or formyl group, by a carboxy group esterified with an alcohol wherein the alcoholic moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group is replaced in the 3- or 4-position by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom that carries a double or triple bond, a $C_{3-8}$-cycloalkyl-$C_{1-3}$-alkanol, a bicycloalkanol with a total of 8 to 10 carbon atoms which is additionally substituted in the bicycloalkyl moiety by one or two $C_{1-3}$-alkyl groups, a 1,3-dihydro-oxo-1-isobenzofuranol or an alcohol of formula $R_a CO$—O—$(R_b CR_c)$—OH, wherein $R_a$ denotes a $C_{1-8}$-alkyl, $C_{5-7}$-cycloalkyl, phenyl or phenyl-$C_{1-3}$-alkyl group, $R_b$ denotes a hydrogen atom, a $C_{1-3}$-alkyl, $C_{5-7}$-cycloalkyl or phenyl group and $R_c$ denotes a hydrogen atom or a $C_{1-3}$-alkyl group, and the imino or amino groups mentioned in the definition of the groups may be substituted by a group which can be cleaved in vivo, e.g. by a hydroxy-$C_{1-8}$-alkoxy, allyloxy, phenyloxy, benzyloxy, 3-methoxybenzyloxy, 4-methylbenzyloxy or 4-chlorophenyl-$C_{1-6}$-alkyloxy group, by an acyl group such as the benzoyl or pyridinoyl group or a $C_{1-16}$-alkanoyl group such as the formyl, acetyl, propionyl, butanoyl, pentanoyl or hexanoyl group, by an allyloxycarbonyl group, by a $C_{1-16}$-alkoxycarbonyl group such as the methyloxycarbonyl, ethyloxycarbonyl, propyloxycarbonyl, isopropyloxycarbonyl, butyloxycarbonyl, tert.butyloxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, by a phenyl-$C_{1-16}$-alkoxycarbonyl group such as the benzyloxycarbonyl, phenylethyloxycarbonyl or phenylpropyloxycarbonyl group, by a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_a CO$—O—$(R_b CR_c)$—O—CO— group wherein $R_a$ to $R_b$ are as hereinbefore defined.

Moreover, the saturated alkyl and alkoxy moieties containing more than 2 carbon atoms mentioned in the definitions above as well as the alkanoyl and unsaturated alkyl moieties which contain more than 3 carbon atoms also include the branched isomers thereof such as the isopropyl, tert.butyl, isobutyl group, etc.

Preferred compounds of general formula I of the present invention are those wherein A denotes an ethynylene or an ethylene group, n denotes one of the numbers 0 or 1, $R_1$ denotes a hydrogen atom, a $C_{1-3}$-alkyl, phenyl, pyridyl or carboxy-$C_{1-3}$-alkyl group, Ar denotes a phenyl or pyridyl group substituted by the groups $R_2$ to $R_4$, while $R_2$ denotes a $C_{1-6}$-alkyl group which may be substituted by a carboxy, amino, $C_{1-3}$-alkylamino, carboxy-$C_{1-3}$-alkylamino, di-($C_{1-3}$-alkyl)-amino, N-(carboxy-$C_{1-3}$-alkyl)-$C_{1-3}$-alkylamino or $C_{3-7}$-cycloalkylamino group, a phenyl, pyridyl or pyrimidyl group which may be substituted by a fluorine, chlorine or bromine atom, by a $C_{1-3}$-alkyl, carboxy-$C_{1-3}$-alkyl, $C_{1-3}$-alkoxy, aminosulphonyl, $C_{1-3}$-alkylsulphonyl or $C_{1-3}$-alkylaminosulphonyl group, a $C_{1-5}$-alkylamino, carboxy-$C_{1-3}$-alkylamino, di-($C_{1-5}$-alkyl)-amino, N-(carboxy-$C_{1-3}$-alkyl)-$C_{1-5}$-alkylamino, $C_{3-7}$-cycloalkylamino or N-(carboxy-$C_{1-3}$-alkyl)-$C_{3-7}$-cycloalkylamino group, a $C_{3-5}$-cycloalkylcarbonylamino, N-($C_{1-3}$-alkyl)-$C_{1-4}$-alkylcarbonylamino or N-($C_{1-3}$-alkyl)-$C_{3-5}$-cycloalkylcarbonylamino group, while the abovementioned N-($C_{1-3}$-alkyl) moieties may additionally be substituted by a carboxy group, a 5- to 7-membered cycloalkyleneimino group, an amino, $C_{1-5}$-alkylamino or $C_{3-7}$-cycloalkylamino group which is substituted in each case at the amino-nitrogen atom by a $C_{1-3}$-alkylcarbonyl or carboxy-$C_{1-3}$-alkylcarbonyl group, while additionally the alkyl moiety of the abovementioned $C_{1-5}$-alkylcarbonyl- and carboxy-$C_{1-3}$-alkylcarbonyl group may be substituted by an amino, hydroxy, carboxy-$C_{1-3}$-alkoxy, carboxy-$C_{1-3}$-alkylaminocarbonyl, carboxy-$C_{1-3}$-alkylamino, N-($C_{1-3}$-alkyl)-carboxy-$C_{1-3}$-alkylamino or amino-$C_{1-3}$-alkylcarbonylamino group, a carbonyl group which is substituted
by a $C_{1-4}$-alkyl or $C_{3-5}$-cycloalkyl group,
by a phenyl group,
by an amino, $C_{1-5}$-alkylamino, $C_{2-5}$-alkenylamino, $C_{3-6}$-alkynylamino, carboxy-$C_{1-3}$-alkylamino or $C_{3-7}$-cycloalkylamino group which may additionally be substituted in each case at the amino-nitrogen atom by a $C_{1-5}$-alkyl group, or
by a $C_{3-6}$-cycloalkyleneimino or $C_{3-6}$-cycloalkenyleneimino group optionally substituted by a $C_{1-3}$-alkyl, carboxy-$C_{1-3}$-alkyl, hydroxy, hydroxy-$C_{1-3}$-alkyl, amino or carboxy group, with the proviso that the hydroxy and the amino groups are not bound in the 2-position, $R_3$ denotes a hydrogen, fluorine, chlorine or bromine atom or a trifluoromethyl group, a $C_{1-3}$-alkoxy, amino, $C_{1-2}$-alkylamino, di-($C_{1-2}$-alkyl)-amino or $C_{1-2}$-alkanoylamino group, a $C_{1-4}$-alkyl, $C_{2-4}$-alkynyl or $C_{3-4}$-cycloalkyl group and $R_4$ denotes a hydrogen atom or a $C_{1-3}$-alkyl group, X denotes an oxygen atom, an imino, N-($C_{1-3}$-alkyl)-imino group, a N-benzyl-imino or N-(pyridyl-$C_{1-3}$-alkyl)-imino group optionally substituted by a carboxy group, a N-($C_{1-3}$-alkyl)-carbonylimino or N-(carboxy-$C_{1-3}$-alkyl)-imino group, $R_5$ denotes a cyano group or an aminomethyl or amidino group optionally substituted by a group which can be cleaved in vivo and $Y_1$ denotes the group $CR^w$,
$Y_2$ denotes the group $CR^x$,
$Y_3$ denotes the group $CR^y$ and
$Y_4$ denotes the group $CR^z$ or
one of the groups $Y_1$ to $Y_4$ denotes a nitrogen atom and the remainder of the groups $Y_1$ to $Y_4$ represent three of the groups $CR^z$ to $CR^z$, while $R^w$, $R^x$, $R^y$ and $R^z$ in each case denote a hydrogen atom or one of the groups $R^w$ to $R^z$ denotes a chlorine atom, a $C_{1-3}$-alkyl group, a hydroxy, $C_{1-3}$-alkoxy, amino or $C_{1-3}$-alkylamino group and the remainder of the groups $R^w$ to $R^z$ in each case represent a hydrogen atom, while particularly those compounds of general formula (I), wherein A denotes the ethynylene group, are of exceptional importance, while the hydrogen atoms in the methyl and methoxy groups mentioned in the definition of the above groups or in the methyl moieties contained in the groups of formula I defined hereinbefore may, unless otherwise stated, be wholly or partially replaced by fluorine atoms, the prodrugs, the tautomers, the stereoisomers, the mixtures thereof and the salts thereof.

Particularly preferred compounds of the present invention are the compounds of general formula Ia

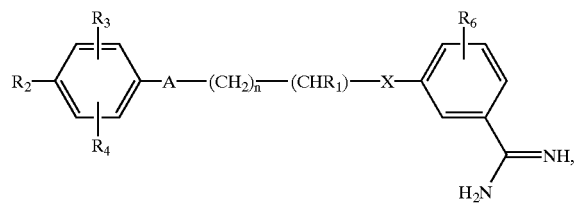

(Ia)

wherein

A denotes an ethylene or ethynylene group, n denotes one of the numbers 0 or 1, $R_1$ denotes a hydrogen atom, a $C_{1-3}$-alkyl, phenyl or carboxy-$C_{1-3}$-alkyl group, $R_2$ denotes a phenyl group which may be substituted by an aminosulphonyl, $C_{1-3}$-alkylsulphonyl or $C_{1-3}$-alkylaminosulphonyl group, a di-($C_{1-5}$-alkyl)-amino, N-(carboxy-$C_{1-3}$-alkyl)-$C_{1-5}$-alkylamino or N-(carboxy-$C_{1-3}$-alkyl)-$C_{3-7}$-cycloalkylamino group, a N-($C_{1-3}$-alkyl)-$C_{1-4}$-alkylcarbonylamino or N-($C_{1-3}$-alkyl)-$C_{3-5}$-cycloalkylcarbonylamino group, a $C_{1-5}$-alkylamino or $C_{3-7}$-cycloalkylamino group which is substituted in each case at the amino-nitrogen atom by a $C_{1-3}$-alkylcarbonyl or carboxy-$C_{1-3}$-alkylcarbonyl group, a carbonyl group which is substituted
by a $C_{1-5}$-alkyl or $C_{3-7}$-cycloalkyl group,
by a phenyl group,
by a $C_{1-5}$-alkylamino, $C_{2-5}$-alkenylamino, $C_{3-6}$-alkynylamino or $C_{3-7}$-cycloalkylamino group which may additionally be substituted in each case at the amino-nitrogen atom by a $C_{1-5}$-alkyl group, or
by a pyrrolidino or 2,5-dihydro-1H-pyrrolyl group optionally substituted by a $C_{1-3}$-alkyl, carboxy-$C_{1-3}$-alkyl, hydroxy, hydroxy-$C_{1-3}$-alkyl, amino or carboxy group, with the proviso that the hydroxy and amino groups are not bound in the 2-position, $R_3$ denotes a hydrogen, fluorine, chlorine or bromine atom or a trifluoromethyl group, a $C_{1-3}$-alkoxy or a $C_{1-4}$-alkyl group and $R_4$ denotes a hydrogen atom or a $C_{1-3}$-alkyl group, X denotes an oxygen atom, an imino, N-($C_{1-3}$-alkyl)-imino, N-benzyl-imino, N-($C_{1-3}$-alkyl)-carbonylimino or N-(carboxy-$C_{1-3}$-alkyl)-imino group, and $R_6$ denotes a chlorine atom or a $C_{1-3}$-alkyl, hydroxy, $C_{1-3}$-alkoxy, amino or $C_{1-3}$-alkylamino group, while particularly those compounds of general formula (Ia), wherein A denotes the ethynylene group, are of exceptional importance, while the hydrogen atoms in the methyl and methoxy groups mentioned in the definition of the above groups or in the methyl moieties contained in the groups of formula Ia defined hereinbefore may, unless otherwise stated, be wholly or partially replaced by fluorine atoms, the prodrugs, the tautomers, the stereoisomers, the mixtures thereof and the salts thereof.

The following may be mentioned as examples of particularly preferred compounds:

(1) 3-{3-[4-(N-acetyl-cyclopentylamino)-3-methyl-phenyl]-propargylamino}-benzamidine,
(2) 4-hydroxy-3-{3-[4-(pyrrolidin-1-yl-carbonyl)-3-methyl-phenyl]-propargylamino}-benzamidine,
(3) 3-{3-[3-methyl-4-(pyrrolidin-1-yl-carbonyl)-phenyl]-propargylamino}-benzamidine,
(4) 3-{N-methyl-3-[3-methyl-4-(pyrrolidin-1-yl-carbonyl)-phenyl]-propargylamino}-benzamidine,
(5) 3-{N-acetyl-3-[3-methyl-4-(pyrrolidin-1-yl-carbonyl)-phenyl]-propargylamino}-benzamidine,
(6) 3-{4-[3-methyl-4-(pyrrolidin-1-yl-carbonyl)-phenyl]-but-3-inylamino}-benzamidine,
(7) 3-{3-[3-methyl-4-(pyrrolidin-1-yl-carbonyl)-phenyl]-propyl-amino}-benzamidine,
(8) 3-{3-[2,5-dimethyl-4-(pyrrolidin-1-yl-carbonyl)-phenyl]-propargylamino}-benzamidine,
(9) 3-[3-(2'-aminosulphonyl-biphenyl-4-yl)-propargylamino]-benzamidine,
(10) 3-{3-[3-methyl-4-(pyrrolidin-1-yl-carbonyl)-phenyl]-propargyl-oxy}-benzamidine,
(11) 3-{1-methyl-3-[3-methyl-4-(pyrrolidin-1-yl-carbonyl)-phenyl]-propargylamino}-benzamidine,
(12) 3-{N-ethoxycarbonylmethyl-3-[3-methyl-4-(pyrrolidin-1-yl-carbonyl)-phenyl]-propargylamino}-benzamidine,
(13) 3-{N-methyl-3-[4-(N-acetyl-cyclopentylamino)-3-methyl-phenyl]-propargylamino}-benzamidine,
(14) 3-{N-hydroxycarbonylmethyl-3-[3-methyl-4-(pyrrolidin-1-yl-carbonyl)-phenyl]-propargylamino}-benzamidine,
(15) 3-{N-methyl-3-{4-[N-(3-ethoxycarbonyl-propionyl)-cyclopentylamino]-3-methyl-phenyl}-propargylamino}-benzamidine,
(16) 3-{N-methyl-3-{4-[N-(2-ethoxycarbonyl-acetyl)-cyclopentylamino]-3-methyl-phenyl}-propargylamino}-benzamidine,
(17) 3-{N-methyl-3-{4-[N-(2-hydroxycarbonyl-acetyl)-cyclopentylamino]-3-methyl-phenyl}-propargylamino}-benzamidine,
(18) 3-{3-[4-(pyrrolidin-1-yl-carbonyl)-phenyl]-propargylamino}-benzamidine,
(19) 3-{N-methyl-3-[3-methyl-4-(pyrrolidin-1-yl-carbonyl)-phenyl]-propyl-amino}-benzamidine,
(20) 3-{N-methyl-3-[3-methyl-4-(2,5-dihydropyrrol-1-yl-carbonyl)-phenyl]-propargylamino}-benzamidine,
(21) 3-{3-[3-methyl-4-(2,5-dihydropyrrol-1-yl-carbonyl)-phenyl]-propargylamino}-benzamidine,
(22) 3-[N-methyl-3-(4-isopropylcarbonyl-3-methyl-phenyl)-propargylamino]-benzamidine,
(23) 3-{N-benzyl-3-[3-methyl-4-(pyrrolidin-1-yl-carbonyl)-phenyl]-propargylamino}-benzamidine,
(24) 3-{N-methyl-3-[3-methyl-4-(N-methyl-propargylamino-carbonyl)-phenyl]-propargylamino}-benzamidine,
(25) 3-{N-methyl-3-[4-(N-allyl-methylamino-carbonyl)-3-methyl-phenyl]-propargylamino}-benzamidine,
(26) 3-{N-methyl-3-[4-(N-ethyl-methylamino-carbonyl)-3-methyl-phenyl]-propargylamino}-benzamidine,
(27) 3-{N-methyl-3-[4-(N-isopropyl-methylamino-carbonyl)-3-methyl-phenyl]-propargylamino}-benzamidine,
(28) 3-{N-methyl-3-[2'-aminosulphonyl-biphenyl-4-yl]-propargylamino}-benzamidine,
(29) 3-[N-methyl-3-(4-diethylaminocarbonyl-3-methyl-phenyl)-propargylamino]-benzamidine,
(30) 3-{N-(2-ethoxycarbonylethyl)-3-[3-methyl-4-(pyrrolidin-1-yl-carbonyl)-phenyl]-propargylamino}-benzamidine,
(31) 3-{N-(2-ethoxycarbonylethyl)-3-[3-methyl-4-(2,5-dihydropyrrol-1-yl-carbonyl)-phenyl]-propargylamino}-benzamidine,
(32) 3-{N-(4-ethoxycarbonylphenylmethyl)-3-[3-methyl-4-(pyrrolidin-1-yl-carbonyl)-phenyl]-propargylamino}-benzamidine,
(33) 3-{N-(3-methoxycarbonylphenylmethyl)-3-[3-methyl-4-(pyrrolidin-1-yl-carbonyl)-phenyl]-propargylamino}-benzamidine,
(34) 3-{N-(4-hydroxycarbonylphenylmethyl)-3-[3-methyl-4-(pyrrolidin-1-yl-carbonyl)-phenyl]-propargylamino}-benzamidine,
(35) 3-{N-(3-hydroxycarbonylphenylmethyl)-3-[3-methyl-4-(pyrrolidin-1-yl-carbonyl)-phenyl]-propargylamino}-benzamidine,
(36) 3-{N-(2-hydroxycarbonylethyl)-3-[3-methyl-4-(pyrrolidin-1-yl-carbonyl)-phenyl]-propargylamino}-benzamidine,
(37) 3-{N-benzyl-3-[3-methyl-4-(2,5-dihydropyrrol-1-yl-carbonyl)-phenyl]-propargylamino}-benzamidine,
(38) 3-[N-benzyl-3-(4-isobutyryl-3-methyl-phenyl)-propargylamino]-benzamidine,
(39) 3-[N-benzyl-3-(4-benzoyl-3-methyl-phenyl)-propargylamino]-benzamidine,
(40) 3-{N-benzyl-3-[2'-aminosulphonyl-biphenyl-4-yl]-propargylamino}-benzamidine,
(41) 3-{N-benzyl-3-[2'-aminosulphonyl-biphenyl-4-yl]-propylamino}-benzamidine,
(42) 3-{N-(pyridin-2-ylmethyl)-3-[3-methyl-4-(pyrrolidin-1-yl-carbonyl)-phenyl]-propargylamino}-benzamidine,
(43) 3-{N-(pyridin-3-ylmethyl)-3-[3-methyl-4-(pyrrolidin-1-yl-carbonyl)-phenyl]-propargylamino}-benzamidine,
(44) 3-[N-(2-ethoxycarbonylethyl)-3-(4-cyclopentylcarbonyl-3-methylphenyl)-propargylamino]-benzamidine and
(45) 3-[N-(4-ethoxycarbonylphenylmethyl)-3-(2'-aminosulphonylbiphenyl-4-yl]-propargylamino]-benzamidine and the salts thereof.

According to the invention the compounds of general formula I are obtained by known methods, for example by the following methods:

a) Reacting a compound of general formula $$Ar-Z_1, \qquad (III)$$

wherein

Ar is as hereinbefore defined and $Z_1$ denotes a leaving group such as a halogen atom or a sulphonyloxy group, e.g. a chlorine, bromine or iodine atom or a trifluoromethylsulphonyloxy group, with a compound of general formula

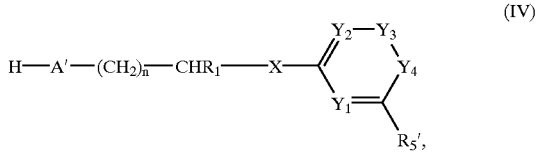

(IV)

wherein

R$_1$, n, Y$_1$, Y$_2$, Y$_3$, Y$_4$ and X are as hereinbefore defined,

R$_5$' has the meanings given for R$_5$ hereinbefore, with the proviso that any amino or imino group present is protected by a conventional protecting group, and A' denotes an ethynyl group, or b) reacting a compound of general formula

Ar—Z$_1$, (III)

wherein

Ar is as hereinbefore defined and

Z$_1$ denotes a leaving group such as a halogen atom or a sulphonyloxy group, e.g. a chlorine, bromine or iodine atom or a trifluoromethylsulphonyloxy group, with a compound of general formula

H—A'—(CH$_2$)$_n$—CHR$_1$—OH, (IV)

wherein n and R$_1$ are as hereinbefore defined and A' denotes an ethynylene group, the reaction product is reacted with 1-bromoprop-2-ene and the resulting compound of formula

Ar—A—(CH$_2$)$_n$—CHR$_1$—Br, (V)

is reacted with a compound of general formula

(IV)

wherein

Y$_1$, Y$_2$, Y$_3$ and Y$_4$ are as hereinbefore defined and R$_5$' has the meanings given for R$_5$ hereinbefore, with the proviso that any amino or imino group present is protected by a conventional protecting group, optionally followed by catalytic hydrogenation and/or cleaving of any protecting group used.

The reaction of an ethynyl compound according to formula III is preferably carried out in a solvent such as acetonitrile, diethyl ether, tetrahydrofuran or dimethylformamide in the presence of a palladium catalyst such as bis(triphenylphosphine)-palladium(II)chloride or tetrakis-(triphenylphosphine)-palladium(0) in the presence of a tertiary or inorganic base such as triethylamine, N-isopropyldiethylamine, potassium tert. butoxide, sodium carbonate or caesium carbonate and in the presence of a reaction accelerator such as a copper halide such as copper(I) iodide and at temperatures between 20 and 120° C., preferably at temperatures between 40 and 100° C., (cf. also K. Sonogashira, Comprehensive Organic Synthesis, Vol. 3, page 52ff., Pergamon Press, Oxford 1991).

The protecting groups optionally used and their removal are described hereinafter (cf. also T. Greene, Protective Groups in Organic Synthesis, Wiley Interscience, New York 1981).

c) To prepare a compound of general formula I wherein the Ar—A group contains a carboxy group and R$_5$ is as hereinbefore defined or the Ar—A group is as hereinbefore defined and R$_5$ denotes an amino, amino-C$_{1-3}$-alkyl or amidino group or the Ar—A group contains a carboxy group and R$_5$ denotes an amino, amino-C$_{1-3}$-alkyl or amidino group:

Converting a compound of general formula

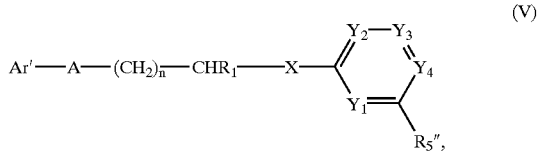

(V)

wherein

A, n, R$_1$, Y$_1$, Y$_2$, Y$_3$, Y$_4$ and X are as hereinbefore defined,

Ar' and R$_5$" have the meanings given for Ar and R$_5$ hereinbefore with the proviso that Ar' contains a group which can be converted into a carboxy group by hydrolysis, treatment with an acid or base, thermolysis or hydrogenolysis and R$_5$" has the meanings given for R$_5$ hereinbefore or Ar' has the meanings given for Ar hereinbefore and R$_5$" denotes a group which can be converted into an amino, amino-C$_{1-3}$-alkyl or amidino group by hydrolysis, treatment with an acid or base, thermolysis or hydrogenolysis or Ar' contains a group which can be converted into a carboxy group by hydrolysis, treatment with an acid or base, thermolysis or hydrogenolysis and R$_5$" contains a group which can be converted into an amino, amino-C$_{1-3}$-alkyl or amidino group by hydrolysis, treatment with an acid or base, thermolysis or hydrogenolysis, by hydrolysis, treatment with an acid or base, thermolysis or hydrogenolysis into a compound of general formula I wherein the Ar—A group contains a carboxy group and R$_5$ is as hereinbefore defined or the Ar—A group is as hereinbefore defined and R$_5$ denotes an amino, amino-C$_{1-3}$-alkyl or amidino group or the Ar—A group contains a carboxy group and R$_5$ denotes an amino, amino-C$_{1-3}$-alkyl or amidino group.

By a group which may be converted into a carboxy group is meant for example a carboxyl group protected by a protecting group, such as the functional derivatives thereof, e.g. the unsubstituted or substituted amides, esters, thioesters, trimethylsilylesters, orthoesters or iminoesters thereof, which may conveniently be converted into a carboxyl group by hydrolysis, the esters thereof with tertiary alcohols, e.g. the tert. butyl ester thereof, which may conveniently be converted into a carboxyl group by treatment with an acid or thermolysis, and the esters thereof with arylalcohols, e.g. the benzyl esters thereof, which may conveniently be converted into a carboxyl group by hydrogenolysis.

The hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

If a compound of general formula V contains the tert.butyl or tert.butyloxycarbonyl group for example, these may also optionally be cleaved by treatment with an acid such as trifluoracetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethyl ether, tetrahydrofuran or dioxane, preferably at temperatures between −10 and 120° C., e.g. at temperatures between 0 and 60° C., or also thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40 and 120° C.

If a compound of general formula V contains the benzyloxy or benzyloxycarbonyl group for example, these may also be cleaved by hydrogenolysis in the presence of a hydrogenation catalyst such as palladium/charcoal in a suitable solvent such as methanol, ethanol, ethanol/water, glacial acetic acid, ethyl acetate, dioxane or dimethylformamide preferably at temperatures between 0 and 50° C., e.g. at ambient temperature, and a hydrogen pressure of 1 to 5 bar.

d) to prepare a compound of general formula I wherein $R_5$ denotes an amidino group:
Reacting a compound of general formula

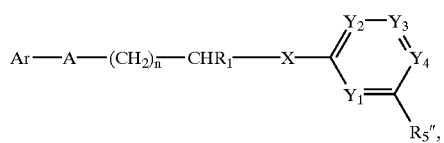
(VI)

optionally formed in the reaction mixture,
wherein
A, Ar, n, $R_1$, $Y_1$, $Y_2$, $Y_3$, $Y_4$ and X are as hereinbefore defined and
$R_5''$ denotes one of the groups mentioned for $R_5$ hereinbefore, with the proviso that $R_5''$ denotes a $Z_1$—(HN=)C— group, wherein
$Z_1$ denotes an alkoxy or arylalkoxy group such as the methoxy, ethoxy, n-propoxy, isopropoxy or benzyloxy group or an alkylthio or arylalkylthio group such as the methylthio, ethylthio, n-propylthio or benzylthio group,
with an ammonium salt such as diammonium carbonate or ammonium acetate.

The reaction is expediently carried out in a solvent such as methanol, ethanol, n-propanol, tetrahydrofuran or dioxane at temperatures between 0 and 150° C., preferably at temperatures between 0 and 80° C.

A compound of general formula VI is obtained, for example, by reacting a corresponding cyano compound with a corresponding alcohol such as methanol, ethanol, n-propanol, isopropanol or benzylalcohol in the presence of an acid such as hydrochloric acid or by reacting a corresponding amide with a trialkyloxonium salt such as triethyloxonium tetrafluoroborate in a solvent such as methylene chloride, tetrahydrofuran or dioxane at temperatures between 0 and 50° C., but preferably at 20° C., or a corresponding nitrile with hydrogen sulphide, conveniently in a solvent such as pyridine or dimethylformamide and in the presence of a base such as triethylamine, and subsequent alkylation of the thioamide formed with a corresponding alkyl or alkylaryl halide.

e) to prepare a compound of general formula I wherein $R_5$ denotes an amidino group which is substituted by a hydroxy or $C_{1-8}$-alkoxy group:
Reacting a compound of general formula

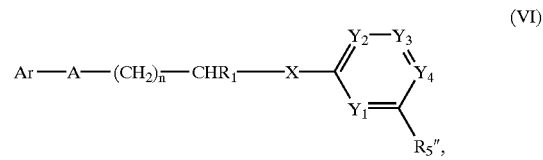
(VI)

optionally formed in the reaction mixture
wherein
A, Ar, n, $Y_1$, $Y_2$, $Y_3$, $Y_4$, $R_1$ and X are as hereinbefore defined and
$R_5''$ denotes one of the groups mentioned for $R_5$ hereinbefore, with the proviso that $R_5''$ denotes a $Z_1$—(HN=)C— group, wherein
$Z_1$ denotes an alkoxy or arylalkoxy group such as the methoxy, ethoxy, n-propoxy, isopropoxy or benzyloxy group or an alkylthio or aralkylthio group such as the methylthio, ethylthio, n-propylthio or benzylthio group,
with hydroxylamine, $C_{1-8}$-alkyloxylamine, allyloxylamine, phenyloxylamine, benzyloxylamine, 3-methoxybenzyloxylamine, 4-methylbenzyloxylamine, 4-chlorophenyl-$C_{1-6}$-alkyloxylamines or the salts thereof.

The reaction is expediently carried out in a solvent such as methanol, ethanol, n-propanol, water, methanol/water, tetrahydrofuran, tetrahydrofuran/water, dioxane or dioxane/water in the presence of a base such as triethylamine at temperatures between 0 and 150° C., preferably at temperatures between 0 and 80° C.

f) to prepare a compound of general formula I wherein X denotes an oxygen or sulphur atom, a carbonyl, imino or N—($C_{1-3}$-alkyl)-imino group:
Reacting a compound of general formula

(VII)

wherein
A, Ar, n and $R_1$ are as hereinbefore defined and
$Z_2$ denotes a leaving group such as a halogen atom or a sulphonyloxy group, e.g. a bromine or iodine atom, a methanesulphonyloxy, trifluoromethanesulphonyloxy or p-toluenesulphonyloxy group, with a compound of general formula

(VIII)

wherein $Y_1$, $Y_2$, $Y_3$, $Y_4$ and $R_5$ are as hereinbefore defined and

U denotes a hydroxy, mercapto, amino, N-phenyl-($C_{1-3}$-alkyl)-amino, N-pyridyl-($C_{1-3}$-alkyl)-amino, N-($C_{1-3}$-alyl)-amino or $C_{1-3}$-alkylcarbonyl-amino group.

The reaction is preferably carried out in a solvent such as methanol, ethanol, methylene chloride, tetrahydrofuran, toluene, dioxane, dimethylsulphoxide or dimethylformamide, optionally in the presence of an inorganic or a tertiary organic base, preferably at temperatures between 20° C. and the boiling temperature of the solvent used.

g) to prepare a compound of general formula I wherein Ar and/or Y contain(s) a group which can be cleaved in vivo:

Reacting a compound of general formula

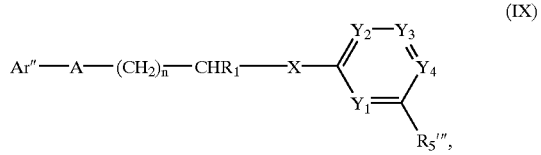

(IX)

wherein

A, n, $R_1$, $Y_1$, $Y_2$, $Y_3$, $Y_4$ and X are as hereinbefore defined, Ar'' and $R_5'''$ have the meanings given for Ar and $R_5$ hereinbefore, with the proviso that Ar'' contains a carboxy group and $R_5'''$ has the meanings given for $R_5$ hereinbefore or Ar'' has the meanings given for Ar hereinbefore and $R_5'''$ contains an amino, amino-$C_{1-3}$-alkyl or amidino group or Ar'' contains a carboxy group and $R_5'''$ contains a group which may be converted into an amino, amino-$C_{1-3}$-alkyl or amidino group, with a compound of general formula

(X)

wherein $R_7$ denotes a $C_{1-8}$-alkoxycarbonyl group, a $R_aCO-O-(R_bCR_c)-$ group or the acyl group of one of the groups mentioned hereinbefore which may be cleaved in vivo, where $R_a$ to $R_c$ are as hereinbefore defined, and $Z_3$ denotes a nucleofugic leaving group such as a halogen atom, e.g. a chlorine, bromine or iodine atom, or a p-nitrophenyl group or also, if Ar'' contains a carboxy group, $Z_3$ denotes a hydroxy group.

The reaction is preferably carried out in a solvent such as methanol, ethanol, methylene chloride, tetrahydrofuran, toluene, dioxane, dimethylsulphoxide or dimethylformamide optionally in the presence of an acid activating agent or a dehydrating agent and optionally in the presence of an inorganic or a tertiary organic base, preferably at temperatures between 20° C. and the boiling temperature of the solvent used.

With a compound of general formula X wherein $Z_3$ denotes a nucleofugic leaving group, the reaction is preferably carried out in a solvent such as methylene chloride, acetonitrile, tetrahydrofuran, toluene, dimethylformamide or dimethylsulphoxide, optionally in the presence of a base such as sodium hydride, potassium carbonate, potassium tert. butoxide or N-ethyl-diisopropylamine at temperatures between 0 and 60° C.

With a compound of general formula X wherein $Z_3$ denotes a hydroxy group, the reaction is optionally carried out in a solvent or mixture of solvents such as methylene chloride, dimethylformamide, benzene, toluene, chlorobenzene, tetrahydrofuran, benzene/tetrahydrofuran or dioxane in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluranium tetrafluoroborate, 2-(1H-benzotriazol-1-yl)-1,1,3,3-tetramethyluronium tetrafluoroborate/1-hydroxybenzotriazole, N,N'-carbonyldiimidazole or triphenylphosphine/carbon tetrachloride, and optionally with the addition of a base such as pyridine, 4-dimethylaminopyridine, N-methylmorpholine or triethylamine, conveniently at temperatures between 0 and 150° C., preferably at temperatures between 0 and 100° C.

If in a compound of general formula X the group $Z_3$ denotes a hydroxy group, the reaction may also be carried out with one of the reactive derivatives thereof such as the esters, imidazolides or halides thereof, preferably in a solvent such as methylene chloride or ether and preferably in the presence of a tertiary organic base such as triethylamine, N-ethyldiisopropylamine or N-methylmorpholine, at temperatures between 0 and 150° C., preferably at temperatures between 50 and 100° C.

If according to the invention a compound of general formula I is obtained wherein $R_5$ denotes an amidino group, this may be converted by alkylation with a haloacetic acid derivative, by subsequent hydrolysis and decarboxylation into a corresponding amidino compound substituted by one or two methyl groups and/or if a compound of general formula I is obtained wherein $R_5$ denotes a hydroxyamidino group, this may be converted by catalytic hydrogenation into a corresponding amidino compound and/or if a compound of general formula I is obtained which contains a double or triple bond, this may be converted by catalytic hydrogenation into a corresponding saturated compound and/or if a compound of general formula I is obtained wherein X denotes a sulphur atom, this may be converted by Oxidation into a corresponding sulphinyl or sulphonyl compound and/or if a compound of general formula I is obtained which contains a carboxy group, this may be converted by means of a corresponding amine into a corresponding amide.

The subsequent alkylation is conveniently carried out in a solvent such as methylene chloride, tetrahydrofuran, dioxane, dimethylsulphoxide, dimethylformamide or acetone, optionally in the presence of a reaction accelerator such as sodium or potassium iodide and preferably in the presence of a base such as sodium carbonate or potassium carbonate or in the presence of a tertiary organic base such as N-ethyldiisopropylamine or N-methylmorpholine, which may simultaneously also serve as solvent, or optionally in the presence of silver carbonate or silver oxide at temperatures between −30 and 100° C., but preferably at temperatures between −10 and 80° C.

The subsequent hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane.

The subsequent decarboxylation is carried out in the presence of an acid as hereinbefore described at temperatures between −10 and 120° C., e.g. at temperatures between ambient temperature and the boiling temperature of the reaction mixture.

The subsequent catalytic hydrogenation is preferably carried out in the presence of a hydrogenation catalyst such as palladium/charcoal and in a suitable solvent such as methanol, ethanol, ethanol/water, glacial acetic acid, ethyl acetate, dioxane or dimethylformamide preferably at temperatures between 0 and 50° C., e.g. at ambient temperature, and at a hydrogen pressure of 1 to 5 bar.

The subsequent oxidation is preferably carried out in a solvent or mixture of solvents, e.g. in water, water/pyridine, acetone, methylene chloride, acetic acid, acetic acid/acetic anhydride, dilute sulphuric acid or trifluoracetic acid, conveniently at temperatures between −80 and 100° C., depending on the oxidising agent used.

To prepare a corresponding sulphinyl compound of general formula I the oxidation is conveniently carried out with one equivalent of the oxidation agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoracetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid, optionally in the presence of a weak base such as sodium acetate, with N-bromosuccinimide in ethanol, with tert.butylhypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphuryl chloride in methylene chloride at −70° C., and the resulting thioether-chlorine complex is conveniently hydrolysed with aqueous ethanol.

To prepare a sulphonyl compound of general formula I, the oxidation is carried out starting from the corresponding sulphinyl compound, conveniently with one or more equivalents of the oxidising agent used or starting from a corresponding sulphenyl compound, conveniently with two or more equivalents of the oxidising agent used, e.g. with hydrogen peroxide in glacial acetic acid/acetic anhydride, trifluoracetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

The subsequent amide formation is preferably carried out in a solvent or mixture of solvents such as methylene chloride, dimethylformamide, benzene, toluene, chlorobenzene, tetrahydrofuran, benzene/tetrahydrofuran or dioxane in the presence of a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium tetrafluoroborate, 2-(1H-benzotriazol-1-yl)-1,1,3,3-tetramethyluronium tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methylmorpholine or triethylamine, conveniently at temperatures between 0 and 150° C., preferably at temperatures between 0 and 100° C.

In the reactions described above any reactive group present such as hydroxy, carboxy, amino, alkylamino or imino groups may be protected during the reaction by conventional protecting groups which are cleaved again after the reaction (cf. also T. Greene, Protective Groups in Organic Synthesis, Wiley Interscience, New York 1981).

For example, a suitable protecting group for a hydroxy group may be the trimethylsilyl, acetyl, benzoyl, tert.butyl, trityl, benzyl or tetrahydropyranyl group, suitable protecting groups for a carboxyl group might be the trimethylsilyl, methyl, ethyl, tert.butyl, benzyl or tetrahydropyranyl group, suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group and a suitable protecting group for an alkynyl group might be the trimethylsilyl group.

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

A trimethylsilyl group is cleaved for example by the addition of tetrabutylammonium fluoride in a solvent such as tetrahydrofuran or by the addition of pyridinium fluoride or using potassium carbonate in methanol.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 3 to 5 bar.

A tert.butyl or tert.butyloxycarbonyl group is preferably cleaved by treating with an acid such as trifluoroacetic acid or hydrochloric acid, optionally using a solvent such as water, methylene chloride, diethyl ether, tetrahydrofuran or dioxane.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae III to X used as starting materials, some of which are known from the literature, are obtained by methods known from the literature and the preparation thereof is also described in the Examples.

For example, a compound of general formula III is either commercially obtainable or can easily be prepared following procedures known from the literature, a compound of general formula IV may be obtained by reacting a corresponding aniline, phenol or thiophenol with a $C_{1-4}$-alkynyl halide, and the compounds of general formulae V, VI, VII and IX may conveniently be obtained by conventional methods as described in the present invention.

Moreover, the compounds of general formula I obtained may be resolved into their enantiomers and/or diastereomers and the compounds of general formula I obtained with a double bond may be resolved into their cis/trans isomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the new compounds of general formula I and the salts thereof have valuable properties.

Thus, the compounds of general formula I wherein $R_5$ does not contain a cyano group have valuable pharmacological properties, particularly an antithrombotic activity which is preferably based on an effect on factor Xa, for example on a factor Xa-inhibiting activity and on an inhibitory effect on related serine proteases such as e.g. thrombin, trypsin, urokinase, factor VIIa, factor IXa, factor XIa and factor XIIa. The compounds of general formula I wherein $R_5$ contains a cyano group constitute valuable intermediate products for preparing the compounds of general formula I wherein $R_5$ denotes an optionally substituted aminomethyl or amidino group.

The compounds of Examples 1 to 45 of the present application were investigated for their effect on the inhibition of factor Xa as follows: Method: Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) of and sodium chloride (150 mMol), pH 8.0

Factor Xa (Roche), spec. activity: 10 U/0.5 ml, final concentration: 0.175 U/ml for each reaction mixture Substrate Chromozym X (Roche), final concentration: 200 $\mu$Mol/l for each reaction mixture Test substance: final concentration 100, 30, 10, 3, 1, 0.3, 0.1, 0.03, 0.01, 0.003, 0.001 $\mu$Mol/l Procedure:

10 $\mu$l of a 23.5-times concentrated starting solution of the test substance or solvent (control), 175 $\mu$l of tris(hydroxymethyl)-aminomethane buffer and 25 $\mu$l of a 1.65 U/ml Factor Xa working solution are incubated for 10 minutes at 37° C. After the addition of 25 $\mu$l of Chromozym X working solution (1.88 $\mu$Mol/l) the sample is measured in a photometer (SpectraMax 250) at 405 nm for 150 seconds at 37° C.

Evaluation:

1. Determining the maximum increase (deltaOD/minutes) over 3 measuring points.

2. Determining the % inhibition based on the solvent control.

3. Plotting a dosage/activity curve (% inhibition vs substance concentration).

4. Determining the $IC_{50}$ by interpolating the X-value (substance concentration) of the dosage/activity curve at Y=50% inhibition.

All the compounds listed in the experimental section had an $IC_{50}$ value <2 $\mu$M.

For example, compound 37 was found to have an $IC_{50}$ value of 4 nM.

The compounds prepared according to the invention are generally well tolerated.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PTCA), and occlusion in peripheral arterial diseases such as pulmonary embolism, disseminated intravascular coagulation, for preventing coronary thrombosis, stroke and the occlusion of shunts. In addition, the compounds according to the invention are suitable for antithrombotic support in thrombolytic treatment, such as for example with alteplase, reteplase, tenecteplase, staphylokinase or streptokinase, for preventing long-term restenosis after PTCA, for the prevention and treatment of ischaemic incidents in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombiant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day. For this purpose, the compounds of formula I prepared according to the invention may be formulated, optionally together with other active substances, with one or more inert conventional carrers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention without restricting its scope:

EXAMPLE 1

3-{3-[4-(N-acetyl-cyclopentylamino)-3-methyl-phenyl]propargylamino}benzamidine-hydrochloride

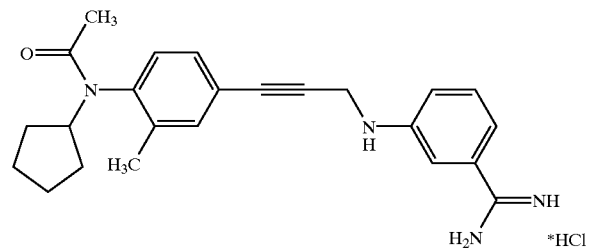

a) 3-propargylamino-benzonitrile 11.8 g (0.1 mol) of 3-aminobenzonitrile and 12.3 ml (0.11 mol) of propargyl bromide (80% in toluene) are stirred in 250 ml toluene and 19.2 ml (0.11 mol) of N-ethyl-diisopropylamine for 18 hours at 90° C. After cooling the mixture is diluted with ethyl acetate and washed with water. The combined organic extracts are dried and concentrated by evaporation. The residue is chromatographed on silica gel, eluting with dichloromethane/ethanol in the ratio 98:2.

Yield: 9.9 g (63% of theory), $R_f$ value: 0.6 (Silica gel; dichloromethane/ethanol=95:5) $C_{10}H_8N_2$ (156.19) Mass spectrum: $(M-H)^-=155$ b) 4-cyclopentylamino-3-methyl-iodobenzene A mixture of 2.5 g (10.7 mmol) of 4-iodo-2-methylaniline, 1.0 ml (11.8 mmol) of cyclo-pentanone, 0.9 ml (16.1 mmol) of glacial acetic acid and 0.1 g of p-toluenesulphonic acid are stirred in 50 ml tetrahydrofuran for 30 minutes. Then 3.1 g (13.9 mmol) of sodium-triacetoxyborohydride are added and the mixture is stirred for a further 26 hours at ambient temperature. The solvent is distilled off and the residue is chromatographed on silica gel, eluting with petroleum ether/ethyl acetate 0 to 10%.

Yield: 0.52 g (16% of theory), $R_f$ value: 0.65 (silica gel; petroleum ether/ethyl acetate=9:1) $C_{10}H16IN$ (301.17) Mass spectrum: $(M+H)^+=302$ c) 4-(N-acetyl-cyclopentylamino)-3-methyl-iodobenzene 0.5 g (1.7 mmol) of 4-cyclopentylamino-3-methyl-iodobenzene are dissolved in 20 ml tetrahydrofuran and after the addition of 81.3 mg (1.7 mmol) of sodium hydride (50% in oil) stirred for 1 hour at 40° C. After cooling to ambient temperature 0.1 ml (1.5 mmol) of acetyl chloride is added and the mixture is stirred overnight at ambient temperature. The solvent is distilled off and the residue distributed in water/ethyl acetate. The combined organic extracts are dried, concentrated by evaporation and chromatographed on silica gel, eluting with dichloromethane/ethanol 0 to 5%.

Yield: 0.30 g (57% of theory), $R_f$ value: 0.40 (silica gel; dichloromethane/ethanol=95:5) $C_{14}H_{18}INO$ (343.21) Mass spectrum: $(M+H)^+=344$ $(M+Na)^+=366$ d) 3-{3-[4-(N-acetyl-cyclopentylamino)-3-methyl-phenyl]-propargylamino}-benzonitrile A mixture of 0.3 g (0.85 mmol) of 4-(N-acetyl-cyclopentylamino)-3-methyl-iodobenzene, 0.4 ml (2.9 mmol) of triethylamine, 97.6 mg (0.08 mmol) of tetrakis-triphenylphospine-palladium(0) and 16.1 mg (0.085 mmol) of copper-(I)-iodide are refluxed in 10 ml acetonitrile for 10 minutes. Then 0.2 g (1.2 mmol) of 3-propargylamino-benzonitrile in 1 ml acetonitrile are added dropwise and refluxed for a further 6 hours. The solvent is distilled off. The residue is taken up in ethyl acetate and washed with 15% sodium chloride solution. The combined organic extracts are concentrated by evaporation and chromatographed on silica gel, eluting with dichloromethane/ethanol 0 to 5%.

Yield: 0.32 g (100% of theory), $R_f$ value: 0.33 (silica gel; dichloromethane/ethanol=95:5) $C_{24}H_{25}N_3O$ (371.49) Mass spectrum: $(M-H)^-=370$ e) 3-{3-[4-(N-acetyl-cyclopentylamino)-3-methyl-phenyl]-propargylamino}benzamidine-hydrochloride A solution of 0.3 g (0.8 mmol) of 3-{3-[4-(N-acetyl-cyclopentyl-amino)-3-methyl-phenyl] propargylamino}benzonitrile is stirred in 30 ml of ethanol saturated with hydrogen chloride gas first for one hour at 0° C. and then for 5 h at ambient temperature. The solvent is removed in vacuo at a maximum bath temperature of 30° C. and replaced by 30 ml of abs. ethanol. Then 0.3 g (2.9 mmol) of ammonium carbonate are added and the mixture is stirred for 36 hours at ambient temperature. The solvent is distilled off and the residue is chromatographed on silica gel, eluting with dichloromethane/ethanol 5 to 25%.

Yield: 0.15 g (42% of theory), $R_f$ value: 0.13 (silica gel; dichloromethane/ethanol=4:1) $C_{24}H_{28}N_4O \times HCl$ (388.52/424.98) Mass spectrum: $(M+H)^+=389$ $(M+Cl)^-=423/25$ (chlorine isotope)

EXAMPLE 2

4-hydroxy-3-{3-[4-(pyrrolidin-1-yl-carbonyl)-3-methyl-phenyl]-propargyl-amino}-benzamidine-hydrochloride

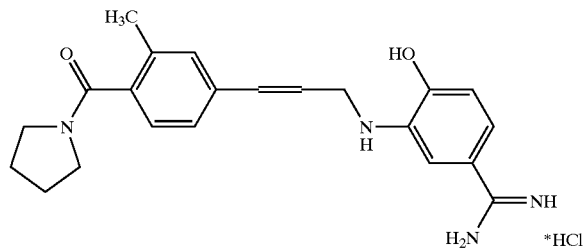

a) 3-methyl-4-(pyrrolidin-1-yl-carbonyl)-bromobenzene 3.2 g (15 mmol) of 4-bromo-2-methyl-benzoic acid are dissolved in 450 ml of tetrahydrofuran and 50 ml of water and after the addition of 1.3 ml (15.4 mmol) of pyrrolidine, 5.3 g (16.5 mmol) of O-(benzotriazol-1-yl)-N,N,N',N'-tetramethyluroniumtetrafluoroborate (tBtU) and 5.7 ml (33 mmol) of N-ethyldiisopropylamine stirred for 19 hours at ambient temperature. The solvent is distilled off, the residue is distributed in dichloromethane/water, the combined organic extracts are dried and concentrated by evaporation. The crude product is chromatographed on silica gel, eluting with dichloromethane/ethanol 0 to 3%.

Yield: 4.0 g (100% of theory), $R_f$ value: 0.46 (silica gel; dichloromethane/ethanol=95:5)

b) 3-[3-methyl-4-(pyrrolidin-1-yl-carbonyl)-phenyl]-propargyl-alcohol

Prepared analogously to Example 1d from 3-methyl-4-(pyrrolidin-1-yl-carbonyl)-bromobenzene, propargylalcohol, tetrakis-triphenyl-phosphine-palladium(0), copper-(I)-iodide and triethylamine in acetonitrile.

Yield: 61% of theory, $R_f$ value: 0.23 (silica gel; dichloromethane/ethanol=95:5) $C_{15}H_{17}NO_2$ (243.31) Mass spectrum: $(M+H)^+=244$ $(M+Na)^+=266$ c) 4-hydroxy-3-{3-[4-(pyrrolidin-1-yl-carbonyl)-3-methyl-phenyl]-propargylamino}-benzonitrile 0.6 g (2.5 mmol) of 3-[3-methyl-4-(pyrrolidin-1-yl-carbonyl)-phenyl]-propargylalcohol and 1 ml (2.7 mmol) of triethylamine are dissolved in 15 ml tetrahydrofuran. At a temperature of 5–10° C. 0.2 ml (2.7 mmol) of methanesulphonic acid chloride are added dropwise in 10 ml tetrahydrofuran. After 10 minutes the reaction is allowed to return to ambient temperature and stirred for a further 1.5 hours. The solution is poured onto ice water and extracted with ethyl acetate. The combined organic extracts are dried and concentrated by evaporation (0.6 g, 78% of theory). The methanesulphonate which is not further purified is dissolved in 10 ml dimethylformamide and after the addition of 0.3 g (2.3 mmol) of 3-amino-4-hydroxybenzonitrile and 1 ml (5.8 mmol) of N-ethyldiisopropylamine stirred for 4 hours at 100° C. Then it is diluted with ethyl acetate and washed with sodium chloride solution. The combined organic extracts are concentrated by evaporation and chromatographed on silica gel, eluting with dichloromethane/ethanol 0 to 5%.

Yield: 0.22 g (32% of theory), $R_f$ value: 0.38 (silica gel; dichloromethane/ethanol=95:5) $C_{22}H_{21}N_3O_2$ (359.43) Mass spectrum: $(M-H)^-=358$ $(M+Na)^+=382$ d) 4-hydroxy-3-{3-[4-(pyrrolidin-1-yl-carbonyl-3-methyl-phenyl]-propargylamino}-benzamidine-hydrochloride Prepared analogously to Example 1e from 4-hydroxy-3-{3-[4-(pyrrolidin-1-yl-carbonyl)-3-methylphenyl]-propargylamino}-benzonitrile, ethanol saturated with hydrogen chloride gas and ammonium carbonate.

Yield: 42% of theory $R_f$ value: 0.07 (silica gel; dichloromethane/ethanol=4:1) $C_{22}H_{24}N_4O_2 \times HCl$ (376.46/412.92) Mass spectrum: $(M-H)^-=375$ $(M+H)^+=377$ $(M+Cl)^-=411/13$ (chlorine isotope)

EXAMPLE 3

3-{3-[3-methyl-4-(pyrrolidin-1-yl-carbonyl)-phenyl]-propargylamino}-benzamidine-hydrochloride

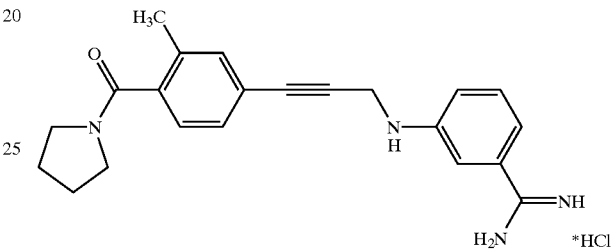

Prepared analogously to Example 1e from 3-{3-[3-methyl-4-(pyrrolidin-1-yl-carbonyl)-phenyl]-propargylamino}-benzonitrile, ethanol saturated with hydrogen chloride gas and ammonium carbonate.

Yield: 24% of theory $R_f$ value: 0.16 (silica gel; dichloromethane/ethanol=4:1) $C_{22}H_{24}N_4O \times HCl$ (360.46/396.92) Mass spectrum: $(M+H)^+=361$ $(M+Cl)^-=395/97$ (chlorine isotope)

EXAMPLE 4

3-{N-methyl-3-[3-methyl-4-(pyrrolidin-1-yl-carbonyl)-phenyl]-propargylamino}-benzamidine-hydrochloride

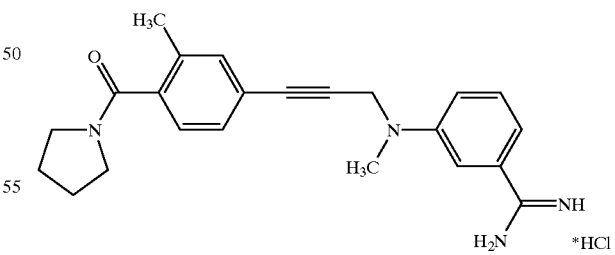

Prepared analogously to Example 1e from 3-{N-methyl-3-[3-methyl-4-(pyrrolidin-1-yl-carbonyl)-phenyl]-propargylamino}-benzonitrile, ethanol saturated with hydrogen chloride gas and ammonium carbonate.

Yield: 43% of theory $R_f$ value: 0.18 (silica gel; dichloromethane/ethanol=4:1) $C_{23}H_{26}N_4 \times HCl$ (374.49/410.95) Mass spectrum: $(M+H)^+=375$ $(M+Cl)^-=409/11$ (chlorine isotope)

EXAMPLE 5

3-{N-acetyl-3-[3-methyl-4-(pyrrolidin-1-yl-carbonyl)-phenyl]-propargylamino}-benzamidine-hydrochloride

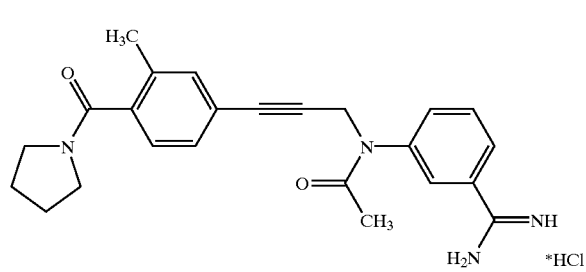

a) 3-(N-acetyl-3-trimethylsilyl-propargylamino)-benzonitrile

Prepared analogously to Example 1c from 3-acetylaminobenzonitrile, 3-trimethylsilyl-propargyl bromide and sodium hydride in tetrahydrofuran.

Yield: 52% of theory $R_f$ value: 0.67 (silica gel; dichloromethane/ethanol=95:5) $C_{15}H_{18}N_2OSi$ (270.41) Mass spectrum: $(M+H)^+=271$ $(M+Na)^+=293$ b) 3-(N-acetyl-propargylamino)-benzonitrile 2.8 g (10.3 mmol) of 3-(N-acetyl-3-trimethylsilyl-propargylamino)-benzonitrile are dissolved in 50 ml of methanol and after the addition of 1.3 g (12.4 mmol) of sodium carbonate stirred for 2 hours. Then the mixture is filtered and the filtrate concentrated by evaporation. The residue is distributed in dichloromethane/water, the combined organic extracts are dried and concentrated by evaporation.

Yield: 1.9 g (91% of theory), $R_f$ value: 0.65 (silica gel; dichloromethane/ethanol=95:5) $C_{12}H_{10}N_2O$ (198.21) Mass spectrum:

$(M)^+=198$ c) 3-{N-acetyl-3-[3-methyl-4-(pyrrolidin-1-yl-carbonyl)-phenyl]-propargylamino}-benzonitrile Prepared analogously to Example 1d from 3-(N-acetyl-propargylamino)-benzonitrile, 3-methyl-4-(pyrrolidin-1-yl-carbonyl)-bromobenzene, tetrakis-triphenylphosphine-palladium(0), copper-(I)-iodide and triethylamine in acetonitrile.

Yield: 31% of theory, $R_f$ value: 0.42 (silica gel; dichloromethane/ethanol=95:5) $C_{24}H_{23}N_3O_2$ (385.47) Mass spectrum: $(M+Na)^+=408$ d) 3-{N-acetyl-3-[3-methyl-4-(pyrrolidin-1-yl-carbonyl)-phenyl]-propargylamino}-benzamidine-hydrochloride Prepared analogously to Example 1e from 3-{N-acetyl-3-[3-methyl-4-(pyrrolidin-1-yl-carbonyl)-phenyl]-propargylamino}-benzonitrile, ethanol saturated with hydrogen chloride gas and ammonium carbonate.

Yield: 73% of theory $R_f$ value: 0.17 (silica gel; dichloromethane/ethanol=4:1) $C_{24}H_{26}N_4O_2 \times HCl$ (402.50/438.97) Mass spectrum: $(M+H)^+=403$ $(M+Cl)^-=437/39$ (chlorine isotope)

EXAMPLE 6

3-{4-[3-methyl-4-(pyrrolidin-1-yl-carbonyl)-phenyl]-but-3-inylamino}-benzamidine-hydrochloride

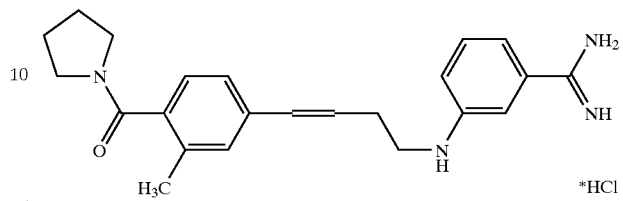

Prepared analogously to Example 1e from 3-{4-[3-methyl-4-pyrrolidin-1-yl-carbonyl)-phenyl]-but-3-inylamino}-benzonitrile, ethanol saturated with hydrogen chloride gas and ammonium carbonate.

Yield: 2% of theory $R_f$ value: 0.15 (silica gel; dichloromethane/ethanol=4:1) $C_{23}H_{26}N_4O \times HCl$ (374.49/410.95) Mass spectrum: $(M+H)^+=375$

EXAMPLE 7

3-{3-[3-methyl-4-(pyrrolidin-1-yl-carbonyl)-phenyl]-propyl-amino}-benzamidine-hydrochloride

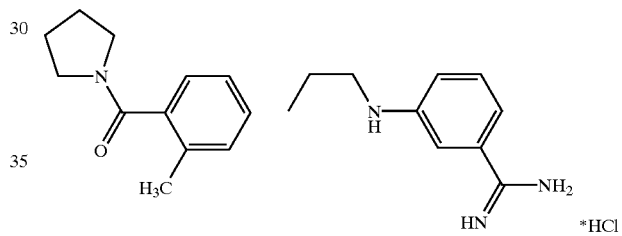

30 mg (75.5 μmol) of 3-{3-[3-methyl-4-pyrrolidin-1-yl-carbonyl)-phenyl]-propargylamino}-benzamidine-hydrochloride are dissolved in 10 ml of ethanol and after the addition of 15 mg of palladium on activated charcoal (10%) at ambient temperature hydrogenated with hydrogen. The catalyst is filtered off and the solution concentrated by evaporation.

Yield: 30 mg (99% of theory), $R_f$ value: 0.17 (silica gel; dichloromethane/ethanol=4:1) $C_{22}H_{28}N_4O \times HCl$ (364.49/400.95) Mass spectrum: $(M)^+=364$ $(M+H)^+=365$ $(M+Cl)^-=399/401$ (chlorine isotope)

EXAMPLE 8

3-{3-[2,5-dimethyl-4-(pyrrolidin-1-yl-carbonyl)-phenyl]-propargylamino}-benzamidine-hydrochloride

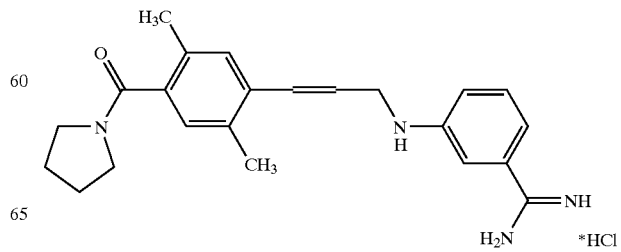

Prepared analogously to Example 1e from 3-{3-[2,5-dimethyl-4-(pyrrolidin-1-yl-carbonyl)-phenyl]-propargylamino}-benzonitrile, ethanol saturated with hydrogen chloride gas and ammonium carbonate.

Yield: 11% of theory $R_f$ value: 0.15 (silica gel; dichloromethane/ethanol=4:1) $C_{23}H_{26}N_4O×HCl$ (374.49/410.95) Mass spectrum: $(M-H)^-=373$ $(M+H)^+=375$ $(M+Cl)^-=409/11$ (chlorine isotope)

EXAMPLE 9

3-[3-(2'-aminosulphonyl-biphenyl-4-yl)-propargylamino]-benzamidine-dihydrochloride

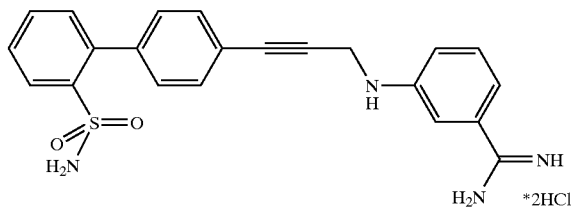

a) N-tert.butyl-benzenesulphonic acid amide 9.6 ml (75 mmol) of benzenesulphonic acid chloride are placed in 100 ml pyridine and 7.9 ml (75 mmol) of tert.butylamine are added dropwise at 5° C., whereupon the temperature increases to 35° C. After the addition has ended the mixture is stirred for another hour at 35° C. Then it is poured onto ice water and the crystalline precipitate is suction filtered.

Yield: 7.8 g (48% of theory), $R_f$ value: 0.75 (silica gel; petroleum ether/ethyl acetate=1:1) $C_{10}H_{15}NO_2S$ (213.30) Mass spectrum: $(M-H)^-=212$ b) 2-tert-butylaminosulphonyl-benzeneboric acid 6.0 g (0.028 mol) of N-tert.butylbenzenesulphonic acid amide are dissolved in 100 ml tetrahydrofuran and at −5° C. 45 ml of n-butyl-lithium (1.6 molar in hexane) are added dropwise. After the addition has ended the mixture is stirred for another hour at ambient temperature. Then 7.2 ml (0.03 mol) of triisopropyl borate in 10 ml tetrahydrofuran are added dropwise and stirred for 1 hour at 35° C. The reaction solution is stirred into 200 ml of 1 molar hydrochloric acid and extracted with ethyl acetate after 30 minutes. The ethyl acetate extracts are extracted with 200 ml of 1 molar sodium hydroxide solution. The alkaline aqueous phases are then extracted with ethyl acetate, the combined organic extracts are dried and concentrated by evaporation. The residue is chromatographed on silica gel, eluting with petroleum ether/ether (25 to 50%).

Yield: 3.3 g (46% of theory), $R_f$ value: 0.2 (silica gel; petroleum ether/ethyl acetate=1:1) $C_{10}H_{16}BNO_4S$ (257.12) Mass spectrum: $(M-H)^-=256$ c) 4'-bromobiphenyl-2-sulphonic acid-tert.-butylamide 0.9 g (3.2 mmol) of 4-bromo-iodobenzene and 0.1 g (0.097 mmol) of tetrakistriphenylphosphine-palladium(0) are stirred in 10 ml of toluene for 10 minutes at ambient temperature. Then 0.5 g (1.9 mmol) of 2-tert.-butylaminosulphonylbenzeneboric acid are dissolved in 15 ml of methanol, 2.4 ml (4.8 mmol) of 2 molar sodium carbonate solution are added and this suspension is added dropwise. The reaction solution is refluxed for 8 hours and stirred overnight at ambient temperature. The organic phase is separated off, extracted again with dichloromethane, the combined organic extracts are dried and concentrated by evaporation. The residue is chromatographed on silica gel, eluting with dichloromethane.

Yield: 0.60 g (52% of theory), $R_f$ value: 0.82 (silica gel; dichloromethane/ethanol=95:5) $C_{16}H_{18}BrNO_2S$ (368.30) Mass spectrum: $(M-H)^-=366/68$ (bromine isotope) $(M+Na)^+=390/92$ (bromine isotope)

d) 3-[3-(2'-tert.butylaminosulphonyl-biphenyl-4-yl-propargylamino]-benzonitrile

Prepared analogously to Example 1d from 4'-bromobiphenyl-2-sulphonic acid-tert.-butylamide, 4-propargylamino-benzonitrile, triethylamine, tetrakis-triphenylphosphine-palladium(0) and copper-(I)-iodide in acetonitrile.

Yield: 39% of theory, $R_f$ value: 0.58 (silica gel; dichloromethane/ethanol=95:5) $C_{26}H_{25}N_3O_2S$ (443.57) Mass spectrum: $(M-H)^-=442$ $(M+Na)^+=466$ e) 3-[3-(2'-aminosulphonyl-biphenyl-4-yl)-propargylamino]-benzamidine-dihydrochloride Prepared analogously to Example 1e from 3-[3-(2'-tert.butyl-aminosulphonyl-biphenyl-4-yl)-propargylamino]-benzonitrile, ethanol saturated with hydrogen chloride gas and ammonium carbonate.

Yield: 33% of theory $R_f$ value: 0.43 (Reversed phase RP 8; methanol/5% sodium chloride solution=6:4) $C_{22}H_{20}N_4O_2S×2$ HCl (404.49/477.41) Mass spectrum: $(M+H)^+=405$ $(M+Cl)^-=439/41$ (chlorine isotope)

EXAMPLE 10

3-{3-[3-methyl-4-(pyrrolidin-1-yl-carbonyl)-phenyl]-propargyl-oxy}-benzamidine-hydrochloride

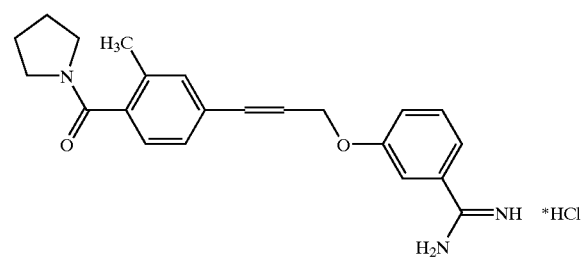

a) 3-{3-[3-methyl-4-(pyrrolidin-1-yl-carbonyl)-phenyl]-propargyl-oxy}-benzonitrile Prepared analogously to Example 2c from 3-[3-methyl-4-(pyrrolidin-1-yl-carbonyl)-phenyl]-propargylalcohol and methanesulphonic acid chloride and subsequent treatment with 3-hydroxybenzonitrile and N-ethyldiisopropylamine in dimethylformamide.

Yield: 64% of theory, $R_f$ value: 0.38 (silica gel; dichloromethane/ethanol=95:5) $C_{22}H_{20}N_2O_2$ (344.42) Mass spectrum: $(M+Na)^+=367$ b) 3-{3-[3-methyl-4-(pyrrolidin-1-yl-carbonyl)-phenyl]-propargyl-oxy}-benzamidine-hydrochloride Prepared analogously to Example 1e from 3-{3-[3-methyl-4-(pyrrolidin-1-yl-carbonyl)-phenyl]-propargyloxy}-benzonitrile, ethanol saturated with hydrogen chloride gas and ammonium carbonate.

Yield: 65% of theory $R_f$ value: 0.19 (silica gel; dichloromethane/ethanol=4:1) $C_{22}H_{23}N_3O_2×HCl$ (361.45/397.92) Mass spectrum: $(M+H)^+=362$ $(M+Cl)^-=396/98$ (chlorine isotope)

EXAMPLE 11

3-{1-methyl-3-[3-methyl-4-(pyrrolidin-1-yl-carbonyl)-phenyl]-propargylamino}-benzamidine-hydrochloride

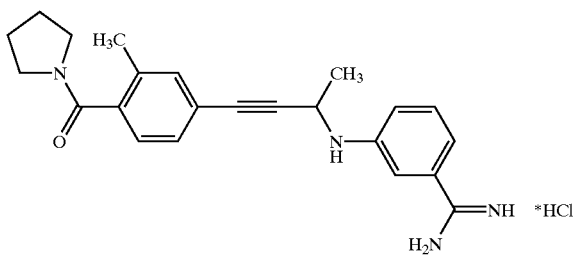

a) 3-methyl-4-(pyrrolidin-1-yl-carbonyl)-bromobenzene

Prepared analogously to Example 2a from 4-bromo-2-methylbenzoic acid, pyrrolidine, tBtU and N-ethyl-diisopropylamine in tetrahydrofuran/water 9:1

Yield: 98% of theory, $R_f$ value: 0.46 (silica gel; dichloromethane/ethanol=95:5) $C_{12}H_{14}BrNO$ (268.15)

b) 1-methyl-3-[3-methyl-4-(pyrrolidin 1-yl-carbonyl)phenyl]-propargylalcohol

Prepared analogously to Example 1d from 3-methyl-4-(pyrrolidin-1-yl-carbonyl)-bromobenzene, 3-butyn-2-ol-tetrakis-triphenyl-phosphine-palladium(0), copper-(I)-iodide and triethylamine in acetonitrile.

Yield: 90% of theory, $R_f$ value: 0.48 (silica gel; dichloromethane/ethanol 95:5) $C_{16}H_{19}NO_2$ (257.33) Mass spectrum: $(M+H)^+=258$ c) 1-methyl-3-[3-methyl-4-(pyrrolidin-1-yl-carbonyl-phenyl]-propargyl-bromide 0.95 g (3.7 mmol) of 1-methyl-3-[3-methyl-4-(pyrrolidin-1-yl-carbonyl)phenyl]-propargyl-alcohol are dissolved in 10 ml acetonitrile and after the addition of 0.66 g (4.0 mmol) of N,N'-carbonyldiimidazole stirred for 30 minutes at ambient temperature. Then 1.6 ml (18.5 mmol) of allylbromide are added and the mixture is refluxed for 3 hours. After cooling to ambient temperature it is diluted with ether. The organic phase is washed with water and saturated sodium chloride solution, dried over sodium sulphate and concentrated by evaporation.

Yield: 1 g (86% of theory) $R_f$ value: 0.5 (silica gel; dichloromethane/ethanol=95:5) $C_{16}H_{18}BrNO$ (320.23) Mass spectrum: $(M+H)^+320/22$ (bromine isotope)

d) 3-{1-methyl-3-[3-methyl-4-(pyrrolidin-1-yl-carbonyl)-phenyl]-propargylamino}-benzonitrile A mixture of 1 g (3.1 mmol) of 1-methyl-3-[3-methyl-4-(pyrrolidin-1-yl-carbonyl)phenyl]-propargyl-bromide, 0.4 g (3.4 mmol) of 3-aminobenzonitrile and 5 ml of N-ethyldiisopropylamine are refluxed in 10 ml tetrahydrofuran for 13 hours. After cooling the mixture is diluted with ethyl acetate, the organic extracts are washed with water, dried over sodium sulphate and concentrated by evaporation. The residue is chromatographed on silica gel, eluting with dichloromethane/methanol 98:2.

Yield: 0.78 g (70% of theory) $R_f$ value: 0.3 (silica gel; dichloromethane/ethanol=95:5) $C_{23}H_{23}N_3O$ (357.46) Mass spectrum: $(M+H)^+=358$ e) 3-{1-methyl-3-[3-methyl-4-(pyrrolidin-1-yl-carbonyl)-phenyl]-propargylamino}-benzamidine-hydrochloride Prepared analogously to Example 1e from 3-{1-methyl-3-[3-methyl-4-(pyrrolidin-1-yl-carbonyl)-phenyl]-propargylamino}-benzonitrile, ethanol saturated with hydrogen chloride gas and ammonium carbonate.

Yield: 67% of theory $R_f$ value: 0.24 (silica gel; dichloromethane/ethanol=4:1) $C_{23}H_{26}N_4O\times HCl$ (374.49/410.95) Mass spectrum: $(M+H)^+=375$ $(M+Cl)^-=409/11$ (chlorine isotope)

EXAMPLE 12

3-{N-ethoxycarbonylmethyl-3-[3-methyl-4-(pyrrolidin-1-yl-carbonyl)-phenyl]-propargylamino}-benzamidine-hydrochloride

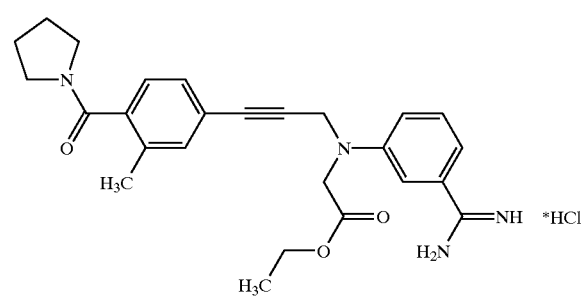

a) 3-(N-ethoxycarbonylmethyl-propargylamino)-benzonitrile

A mixture of 0.78 g (5 mmol) of 3-propargylamino-benzonitrile, 0.55 ml (5 mmol) of ethyl bromoacetate and 0.2 g (5 mmol) of magnesium oxide are stirred in 20 ml of dimethylacetamide for 6 days at 75° C. Then the mixture is filtered, the filtrate is diluted with ethyl acetate and washed with water. The combined organic extracts are dried and concentrated by evaporation. The residue is chromatographed on silica gel, eluting with dichloromethane.

Yield: 1 g (83% of theory) $R_f$ value: 0.61 (silica gel; dichloromethane/ethanol=95:5) $C_{14}H_{14}N_2O_2$ (242.28) Mass spectrum: $(M+H)^+=243$ b) 3-{N-ethoxycarbonylmethyl-3-[3-methyl-4-(pyrrolidin-1-yl-carbonyl)-phenyl]-propargylamino}-benzonitrile Prepared analogously to Example 1d from 3-(N-ethoxycarbonylethyl-N-propargylamino)-benzonitrile, 3-methyl-4-(pyrrolidin-1-yl-carbonyl)-iodobenzene, tetrakis-triphenyl-phosphine-palladium(0), copper-(I)-iodide and triethylamine in acetonitrile. The crude product was further reacted directly $R_f$ value: 0.43 (silica gel; dichloromethane/ethanol=95:5) $C_{26}H_{27}N_3O_3$ (429.52) Mass spectrum: $(M+H)^+=430$ c) 3-{N-ethoxycarbonylmethyl-3-[3-methyl-4-(pyrrolidin-1-yl-carbonyl)-phenyl]-propargylamino}-benzamidine-hydrochloride Prepared analogously to Example 1e from 3-{N-ethoxycarbonylmethyl-3-[3-methyl-4-(pyrrolidin-1-yl-carbonyl)-phenyl]-propargylamino}-benzonitrile, ethanol saturated with hydrogen chloride gas and ammonium carbonate.

Yield: 21% of theory $R_f$ value: 0.1 (silica gel; dichloromethane/ethanol=4:1) $C_{26}H_{30}N_4O_3\times HCl$ (446.56/483.02) Mass spectrum: $(M+H)^+=447$ $(M+Cl)^-=481/83$ (chlorine isotope)

EXAMPLE 13

3-{N-methyl-3-[4-(N-acetyl-cyclopentylamino)-3-methyl-phenyl]propargylamino}-benzamidine-hydrochloride

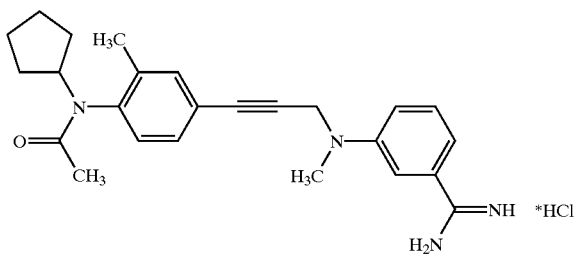

Prepared analogously to Example 1e from 3-{N-methyl-3-[4-(N-acetyl-cyclopentylamino)-3-methyl-phenyl]propargylamino}benzonitrile, ethanol saturated with hydrogen chloride gas and ammonium carbonate.

Yield: 30% of theory $R_f$ value: 0.15 (silica gel; dichloromethane/ethanol=4:1) $C_{25}H_{30}N_4O \times HCl$ (402.55/439.01) Mass spectrum: $(M+H)^+=403$ $(M+Cl)^-=437/39$ (chlorine isotope)

EXAMPLE 14

3-{N-hydroxycarbonylmethyl-3-[3-methyl-4-(pyrrolidin-1-yl-carbonyl)-phenyl]-propargylamino}-benzamidine-hydrochloride

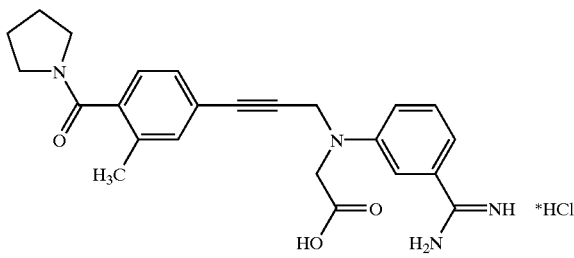

0.3 g (0.62 mmol) of 3-{N-ethoxycarbonylmethyl-3-[3-methyl-4-(pyrrolidin-1-yl-carbonyl)-phenyl]-propargylamino}-benzamidine-hydrochloride are stirred in 10 ml of 6 molar hydrochloric acid for 4 days at ambient temperature. The hydrochloric acid is distilled off.

Yield: 0.28 g (99% of theory) $R_f$ value: 0.52 (Reversed phase RP 8; methanol/5% sodium chloride solution=6:4) $C_{24}H_{26}N_4O_3 \times HCl$ (418.50/454.96) Mass spectrum: $(M+H)^+=419$ $(M-H)^-=417$

EXAMPLE 15

3-{N-methyl-3-{4-[N-(3-ethoxycarbonyl-propionyl)-cyclopentylamino]-3-methyl-phenyl}-propargylamino}benzamidine-hydrochloride

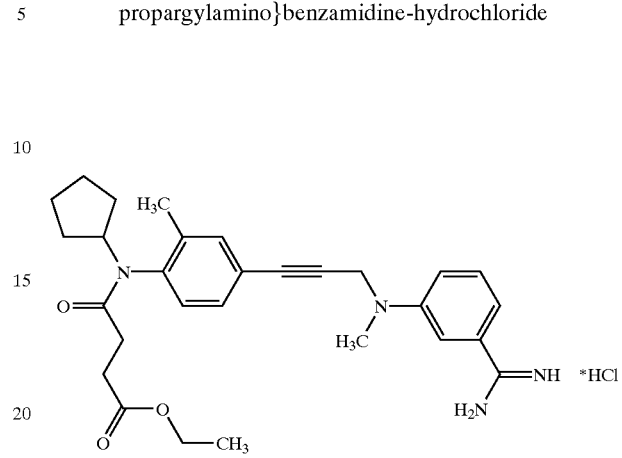

Prepared analogously to Example 1e from 3-{N-methyl-3-{4-[N-(3-ethoxycarbonyl-propionyl)-cyclopentylamino]-3-methyl-phenyl}propargylamino}benzonitrile, ethanol saturated with hydrogen chloride gas and ammonium carbonate.

Yield: 45% of theory $R_f$ value: 0.34 (silica gel; dichloromethane/ethanol=4:1) $C_{29}H_{36}N_4O_3 \times HCl$ (488.65/525.10) Mass spectrum: $(M+H)^+=489$

EXAMPLE 16

3-{N-methyl-3-{4-[N-(2-ethoxycarbonyl-acetyl)-cyclopentylamino]-3-methyl-phenyl}propargylamino}benzamidine-hydrochloride

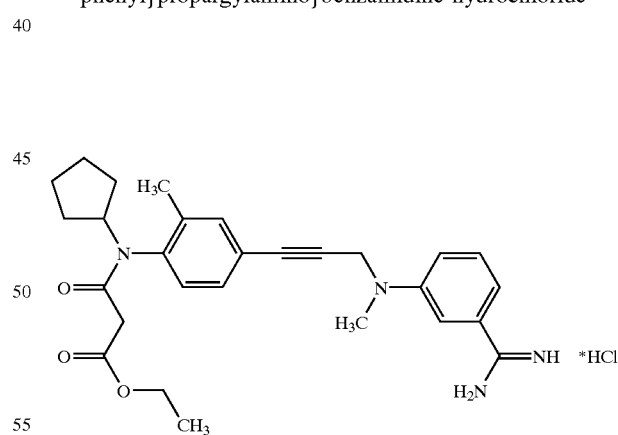

Prepared analogously to Example 1e from 3-{N-methyl-3-{4-[N-(2-ethoxycarbonyl-acetyl)-cyclopentylamino]-3-methyl-phenyl}propargylamino}benzonitrile, ethanol saturated with hydrogen chloride gas and ammonium carbonate.

Yield: 67% of theory $R_f$ value: 0.23 (silica gel; dichloromethane/ethanol=4:1) $C_{28}H_{34}N_4O_3 \times HCl$ (474.61/511.07) Mass spectrum: $(M+H)^+=475$
$(M+Cl)^-=509/11$ (chlorine isotope)

EXAMPLE 17

3-{N-methyl-3-{4-[N-(2-hydroxycarbonyl-acetyl)-cyclopentylamino]-3-methyl-phenyl}-propargylamino}benzamidine-hydrochloride

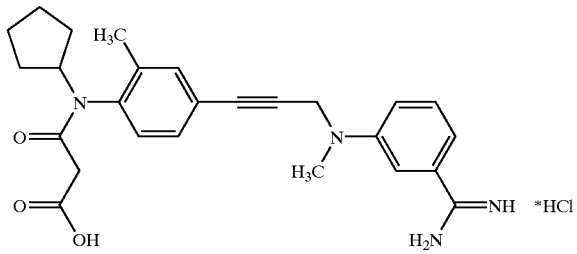

Prepared analogously to Example 14 from 3-{N-methyl-3-{4-[N-(2-ethoxycarbonyl-acetyl)-cyclopentylamino]-3-methyl-phenyl}propargylamino}benzamidine-hydrochloride and 6 molar hydrochloric acid.

Yield: 100% of theory $R_f$ value: 0.43 (Reversed phase RP 8; methanol/5% sodium chloride solution=6:4) $C_{26}H_{30}N_4O_3 \times HCl$ (446.56/483.02) Mass spectrum: $(M+H)^+=447$ $(M-H)^-=445$ $(M+Cl)^-=481/83$ (chlorine isotope)

EXAMPLE 18

3-{3-[4-(pyrrolidin-1-yl-carbonyl)-phenyl]-propargylamino}-benzamidine-hydrochloride

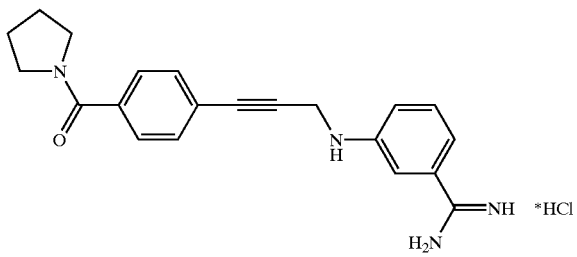

Prepared analogously to Example 1e from 3-{3-[4-(pyrrolidin-1-yl-carbonyl)-phenyl]-propargylamino}-benzonitrile, ethanol saturated with hydrogen chloride gas and ammonium carbonate.

Yield: 54% of theory $R_f$ value: 0.15 (silica gel; dichloromethane/ethanol=4:1) $C_{21}H_{22}N_4O \times HCl$ (346.44/382.90) Mass spectrum: $(M+H)^+=347$ $(M+Cl)^-=381/83$ (chlorine isotope)

EXAMPLE 19

3-{N-methyl-3-[3-methyl-4-(pyrrolidin-1-yl-carbonyl)-phenyl]-propyl-amino}-benzamidine-hydrochloride

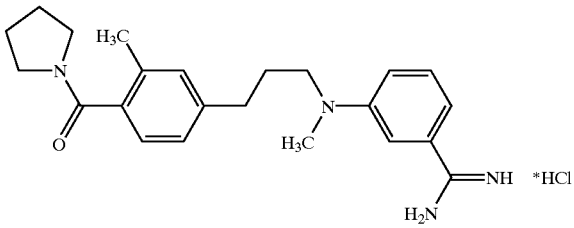

Prepared analogously to Example 7 from 3-{N-methyl-3-[3-methyl-4-(pyrrolidin-1-yl-carbonyl)-phenyl]-propargylamino}-benzamidine-hydrochloride, palladium on activated charcoal (10%) and hydrogen in ethanol.

Yield: 84% of theory $R_f$ value: 0.15 (silica gel; dichloromethane/ethanol=4:1) $C_{23}H_{30}N_4O \times HCl$ (378.53/414.99) Mass spectrum: $(M+H)^+=379$ $(M+Cl)^-=413/15$ (chlorine isotope)

EXAMPLE 20

3-{N-methyl-3-[3-methyl-4-(2,5-dihydropyrrol-1-yl-carbonyl)-phenyl]-propargylamino}-benzamidine-hydrochloride

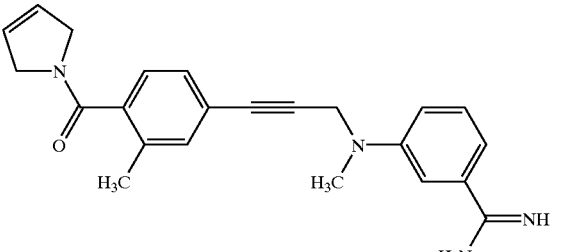

Prepared analogously to Example 1e from 3-{N-methyl-3-[3-methyl-4-(2,5-dihydropyrrol-1-yl-carbonyl)-phenyl]-propargylamino}-benzonitrile, ethanol saturated with hydrogen chloride gas and ammonium carbonate.

Yield: 83% of theory $R_f$ value: 0.16 (silica gel; dichloromethane/ethanol=4:1) $C_{23}H_{24}N_4O \times HCl$ (372.48/408.94) Mass spectrum: $(M+H)^+=373$ $(M+Cl)^-=407/09$ (chlorine isotope)

EXAMPLE 21

3-{3-[3-methyl-4-(2,5-dihydropyrrol-1-yl-carbonyl)-phenyl]-propargylamino}-benzamidine-hydrochloride

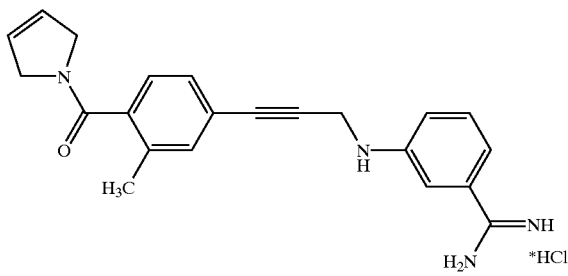

Prepared analogously to Example 1e from 3-{3-[3-methyl-4-(2,5-dihydropyrrol-1-yl-carbonyl)-phenyl]-propargylamino}-benzonitrile, ethanol saturated with hydrogen chloride gas and ammonium carbonate.

Yield: 22% of theory $R_f$ value: 0.15 (silica gel; dichloromethane/ethanol=4:1) $C_{22}H_{22}N_4O\times HCl$ (358.45/394.91) Mass spectrum: $(M+H)^+=359$ $(M+Cl)^-=393/95$ (chlorine isotope)

EXAMPLE 22

3-[N-methyl-3-(4-isopropylcarbonyl-3-methyl-phenyl)-propargylamino]-benzamidine-hydrochloride

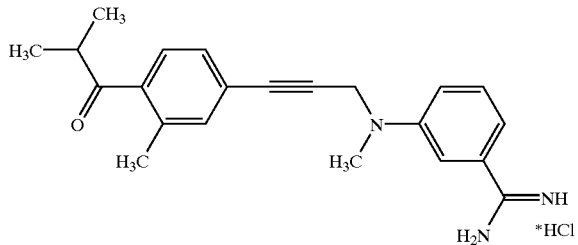

a) 4-isopropylcarbonyl-3-methyl-bromobenzene 0.58 g (24 mmol) of magnesium fragments are added to 10 ml diethyl ether, then 2 ml (21.3 mmol) of isopropyl bromide followed by 2 g (10 mmol) of 4-bromo-2-methyl-benzonitrile in 10 ml diethyl ether are added dropwise. The reaction mixture is maintained at ambient temperature for 1 h and refluxed for 15 hours. After cooling, it is carefully combined with ice water and acidified with 1 molar sulphuric acid. Then it is stirred for 1 hour at 80° C., cooled and extracted with dichloromethane. The combined organic extracts are dried over sodium sulphate and concentrated by evaporation.

Yield: 2.3 g (96% of theory) $R_f$ value: 0.14 (Reversed phase RP 8; methanol/5% sodium chloride solution=6:4) $C_{11}H_{13}BrO$ (241.13) Mass spectrum: $(M+H)^+=241/43$ (bromine isotope)

b) 3-[N-methyl-3-(4-isopropylcarbonyl-3-methyl-phenyl)-propargylamino]-benzonitrile Prepared analogously to Example 1d from 4-isopropylcarbonyl-3-methyl-bromobenzene, 3-(methyl-propargylamino)-benzonitrile, tetrakis-triphenylphosphine-palladium (0), copper-(I)-iodide and triethylamine in acetonitrile.

Yield: 27% of theory $R_f$ value: 0.64 (silica gel; dichloromethane/ethanol=98:2) $C_{22}H_{22}N_2O$ (330.43) Mass spectrum: $(M+H)^+=331$ $(M+Na)^+=353$ c) 3-[N-methyl-3-(4-isopropylcarbonyl-3-methyl-phenyl)-propargylamino]-benzamidine-hydrochloride Prepared analogously to Example 1e from 3-[N-methyl-3-(4-isopropylcarbonyl-3-methyl-phenyl)-propargylamino]-benzonitrile, ethanol saturated with hydrogen chloride gas and ammonium carbonate.

Yield: 65% of theory $R_f$ value: 0.31 (silica gel; dichloromethane/ethanol=4:1) $C_{22}H_{25}N_3O\times HCl$ (347.47/383.93) Mass spectrum: $(M+H)^+=348$ $(M+Cl)^-=382/84$ (chlorine isotope)

EXAMPLE 23

3-{N-benzyl-3-[3-methyl-4-(pyrrolidin-1-yl-carbonyl)-phenyl]-propargylamino}-benzamidine-hydrochloride

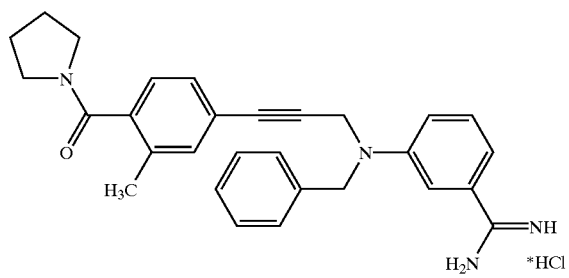

Prepared analogously to Example 1e from 3-{N-benzyl-3-[3-methyl-4-(pyrrolidin-1-yl-carbonyl)-phenyl]-propargylamino}-benzonitrile, ethanol saturated with hydrogen chloride gas and ammonium carbonate.

Yield: 50% of theory $R_f$ value: 0.27 (silica gel; dichloromethane/ethanol=4:1) $C_{29}H_{30}N_4O\times HCl$ (450.60/487.05) Mass spectrum: $(M+H)^+=451$ $(M+Cl)^-=485/87$ (chlorine isotope)

EXAMPLE 24

3-{N-methyl-3-[3-methyl-4-(N-methyl-propargylamino-carbonyl)-phenyl]-propargyl-amino}-benzamidine-hydrochloride

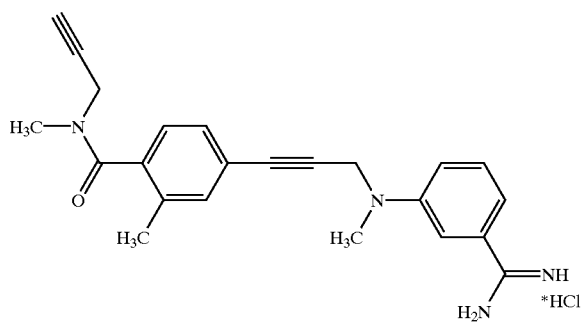

Prepared analogously to Example 1e from 3-{N-methyl-3-[3-methyl-4-(N-methyl-propargylamino-carbonyl)-phenyl]-propargylamino}-benzonitrile, ethanol saturated with hydrogen chloride gas and ammonium carbonate.

Yield: quantitative $R_f$ value: 0.19 (silica gel; dichloromethane/ethanol=4:1) $C_{23}H_{24}N_4O \times HCl$ (372.48/408.94) Mass spectrum: $(M+H)^+=373$

EXAMPLE 25

3-{N-methyl-3-[4-(N-allyl-methylamino-carbonyl)-3-methyl-phenyl]-propargylamino}-benzamidine-hydrochloride

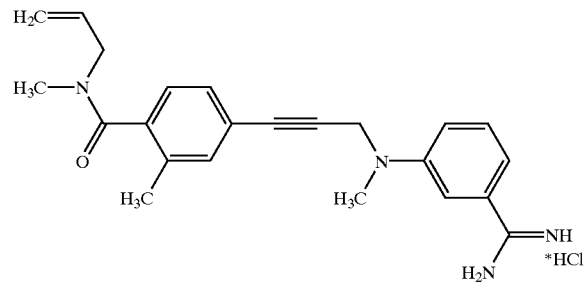

Prepared analogously to Example 1e from 3-{N-methyl-3-[4-(N-allyl-methylamino-carbonyl)-3-methyl-phenyl]-propargylamino}-benzonitrile, ethanol saturated with hydrogen chloride gas and ammonium carbonate.

Yield: quantitative $R_f$ value: 0.23 (silica gel; dichloromethane/ethanol=4:1) $C_{23}H_{26}N_4O \times HCl$ (374.50/410.95) Mass spectrum: $(M+H)^+=375$

EXAMPLE 26

3-{N-methyl-3-[4-(N-ethyl-methylamino-carbonyl)-3-methyl-phenyl]-propargylamino}-benzamidine-hydrochloride

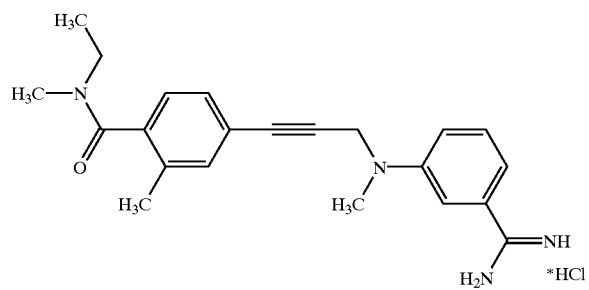

Prepared analogously to Example 1e from 3-{N-methyl-3-[4-(N-ethyl-methylamino-carbonyl-3-methyl-phenyl]-propargylamino}-benzonitrile, ethanol saturated with hydrogen chloride gas and ammonium carbonate.

Yield: quantitative $R_f$ value: 0.19 (silica gel; dichloromethane/ethanol=4:1) $C_{22}H_{26}N_4O \times HCl$ (362.48/398.94) Mass spectrum: $(M+H)^+=363$

EXAMPLE 27

3-{N-methyl-3-[4-(N-isopropyl-methylamino-carbonyl)-3-methyl-phenyl]-propargyl-amino}-benzamidine-hydrochloride

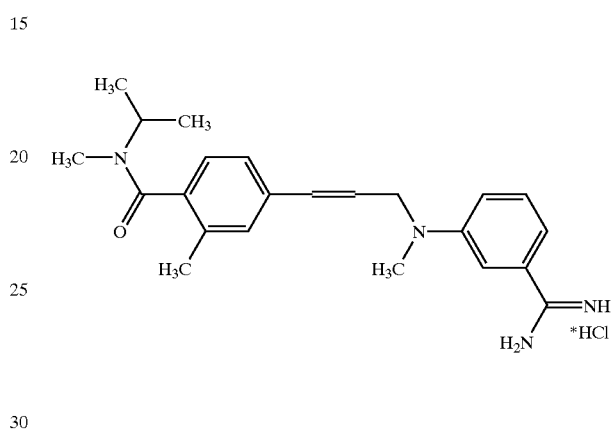

Prepared analogously to Example 1e from 3-{N-methyl-3-[4-(N-isopropyl-methylamino-carbonyl)-3-methyl-phenyl]-propargylamino}-benzonitrile, ethanol saturated with hydrogen chloride gas and ammonium carbonate.

Yield: 66% of theory $R_f$ value: 0.1 (silica gel; dichloromethane/ethanol=9:1) $C_{23}H_{28}N_4O \times HCl$ (376.51/412.97) Mass spectrum: $(M+H)^+=376$

EXAMPLE 28

3-{N-methyl-3-[2'-aminosulphonyl-biphenyl-4-yl]-propargylamino}-benzamidine-hydrochloride

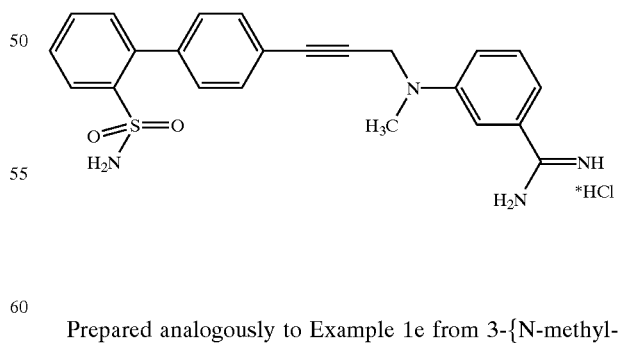

Prepared analogously to Example 1e from 3-{N-methyl-3-[2'-tert.butylaminosulphonyl-biphenyl-4-yl]-propargylamino}-benzonitrile, ethanol saturated with hydrogen chloride gas and ammonium carbonate.

Yield: quantitative $R_f$ value: 0.13 (silica gel; dichloromethane/ethanol=9:1) $C_{23}H_{22}N_4O_2S \times HCl$ (418.53/454.99) Mass spectrum: $(M+H)^+=419$ $(M-H)^-=417$

EXAMPLE 29

3-[N-methyl-3-(4-diethylaminocarbonyl-3-methyl-phenyl)-propargylamino]-benzamidine-hydrochloride

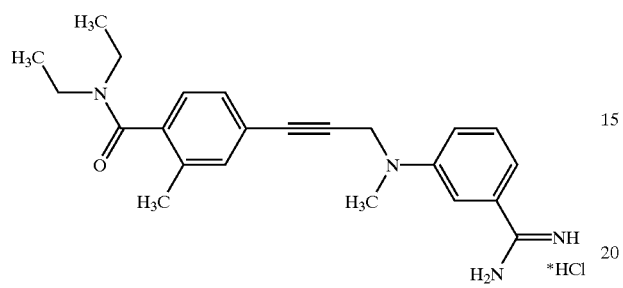

Prepared analogously to Example 1e from 3-[N-methyl-3-(4-diethylaminocarbonyl-3-methyl-phenyl)-propargylamino]-benzonitrile, ethanol saturated with hydrogen chloride gas and ammonium carbonate.

Yield: 8% of theory $R_f$ value: 0.29 (silica gel; dichloromethane/ethanol=4:1) $C_{23}H_{28}N_4O \times HCl$ (376.51/412.97) Mass spectrum: $(M+H)^+=377$

EXAMPLE 30

3-{N-(2-ethoxycarbonylethyl)-3-[3-methyl-4-(pyrrolidin-1-yl-carbonyl)-phenyl]-propargylamino}-benzamidine-hydrochloride

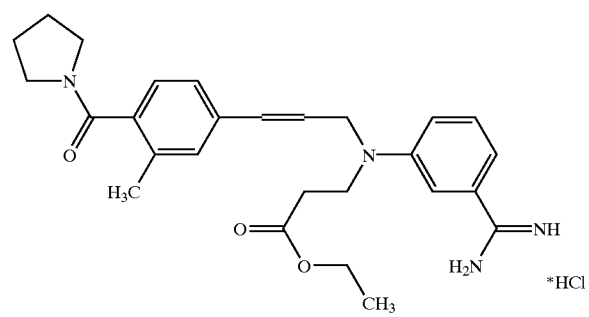

Prepared analogously to Example 1e from 3-{N-(2-ethoxycarbonylethyl)-3-[3-methyl-4-(pyrrolidin-1-yl-carbonyl)-phenyl]-propargylamino}-benzonitrile, ethanol saturated with hydrogen chloride gas and ammonium carbonate.

Yield: 52% of theory $R_f$ value: 0.22 (silica gel; dichloromethane/ethanol=4:1) $C_{27}H_{32}N_4O_3 \times HCl$ (460.59/497.05) Mass spectrum: $(M+H)^+=461$ $(M+Cl)^-=495/97$ (chlorine isotope)

EXAMPLE 31

3-{N-(2-ethoxycarbonylethyl)-3-[3-methyl-4-(2,5-dihydropyrrol-1-yl-carbonyl)-phenyl]-propargylamino}-benzamidine-hydrochloride

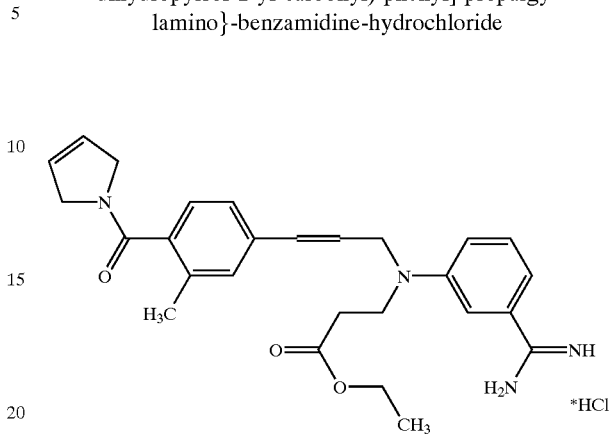

Prepared analogously to Example 1e from 3-{N-(2-ethoxycarbonylethyl)-3-[3-methyl-4-(2,5-dihydropyrrol-1-yl-carbonyl)-phenyl]-propargylamino}-benzonitrile, ethanol saturated with hydrogen chloride gas and ammonium carbonate.

Yield: 49% of theory $R_f$ value: 0.22 (silica gel; dichloromethane/ethanol 4:1) $C_{27}H_{30}N_4O_3 \times HCl$ (458.57/495.03) Mass spectrum: $(M+H)^+=459$ $(M+Cl)^-=493/95$ (chlorine isotope)

EXAMPLE 32

3-{N-(4-ethoxycarbonylphenylmethyl)-3-[3-methyl-4-(pyrrolidin-1-yl-carbonyl)-phenyl]-propargylamino}-benzamidine-hydrochloride

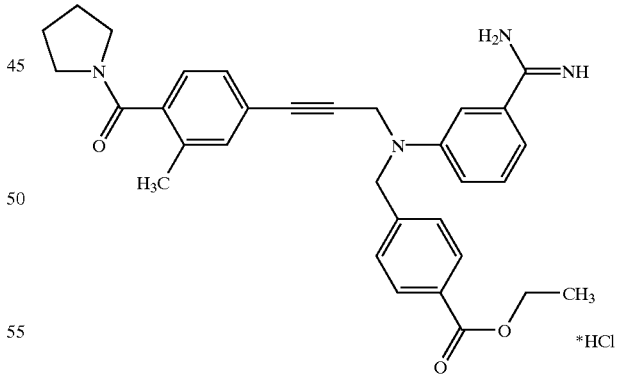

Prepared analogously to Example 1e from 3-{N-(4-ethoxycarbonylphenylmethyl)-3-[3-methyl-4-(pyrrolidin-1-yl-carbonyl)-phenyl]-propargylamino}-benzonitrile, ethanol saturated with hydrogen chloride gas and ammonium carbonate.

Yield: 38% of theory $R_f$ value: 0.38 (silica gel; dichloromethane/ethanol=4:1) $C_{32}H_{34}N_4O_3 \times HCl$ (522.66/559.12) Mass spectrum: $(M+H)^+=523$ $(M+Cl)^-=557$

EXAMPLE 33

3-{N-(3-methoxycarbonylphenylmethyl)-3-[3-methyl-4-(pyrrolidin-1-yl-carbonyl)-phenyl]-propargylamino}-benzamidine-hydrochloride

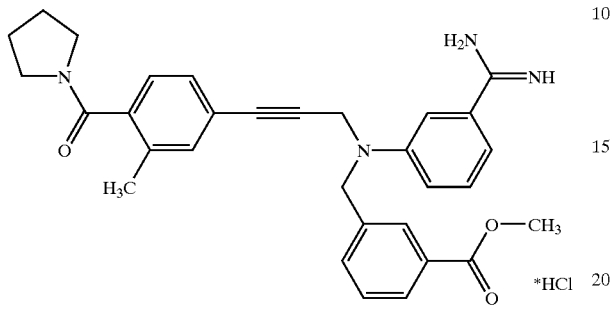

Prepared analogously to Example 1e from 3-{N-(3-methoxycarbonylphenylmethyl)-3-[3-methyl-4-(pyrrolidin-1-yl-carbonyl)-phenyl]-propargylamino}-benzonitrile, ethanol saturated with hydrogen chloride gas and ammonium carbonate.

Yield: 71% of theory $R_f$ value: 0.28 (silica gel; dichloromethane/ethanol=4:1) $C_{31}H_{32}N_4O_3 \times HCl$ (508.64/545.09) Mass spectrum: $(M+H)^+=509$ $(M+Cl)^-=543/45$ (chlorine isotope)

EXAMPLE 34

3-{N-(4-hydroxycarbonylphenylmethyl)-3-[3-methyl-4-(pyrrolidin-1-yl-carbonyl)-phenyl]-propargylamino}-benzamidine-hydrochloride

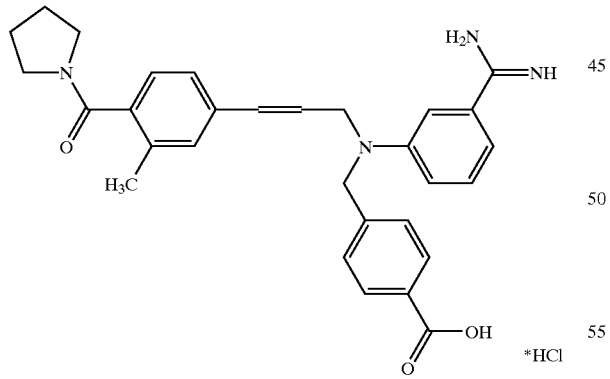

Prepared analogously to Example 14 from 3-{N-(4-ethoxycarbonylphenylmethyl)-3-[3-methyl-4-(pyrrolidin-1-yl-carbonyl)-phenyl]-propargylamino}-benzamidine-hydrochloride and 6 molar hydrochloric acid.

Yield: quantitative $R_f$ value: 0.25 (Reversed phase RP 8; methanol/5% sodium chloride solution=6:4) $C_{30}H_{30}N_4O_3 \times HCl$ (494.61/531.06) Mass spectrum: $(M+H)^+=495$ $(M-H)^-=493$

EXAMPLE 35

3-{N-(3-hydroxycarbonylphenylmethyl)-3-[3-methyl-4-(pyrrolidin-1-yl-carbonyl)-phenyl]-propargylamino}-benzamidine-hydrochloride

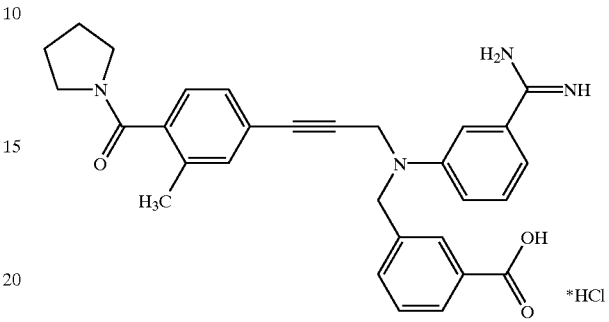

Prepared analogously to Example 14 from 3-{N-(3-methoxycarbonylphenylmethyl)-3-[3-methyl-4-(pyrrolidin-1-yl-carbonyl)-phenyl]-propargylamino}-benzamidine-hydrochloride and 6 molar hydrochloric acid. Yield: 69% of theory $R_f$ value: 0.24 (Reversed phase RP 8; methanol/5% sodium chloride solution=6:4) $C_{30}H_{30}N_4O_3 \times HCl$ (494.61/531.06) Mass spectrum: $(M+H)^+=495$ $(M-H)^-=493$

EXAMPLE 36

3-{N-(2-hydroxycarbonylethyl)-3-[3-methyl-4-(pyrrolidin-1-yl-carbonyl)-phenyl]-propargylamino}-benzamidine-hydrochloride

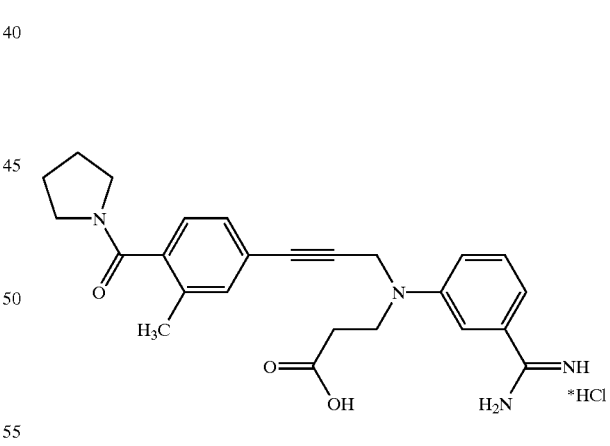

Prepared analogously to Example 14 from 3-{N-(2-ethoxycarbonylethyl)-3-[3-methyl-4-(pyrrolidin-1-yl-carbonyl)-phenyl]-propargylamino}-benzamidine-hydrochloride and 6 molar hydrochloric acid.

Yield: quantitative $R_f$ value: 0.41 (Reversed phase RP 8; methanol/5% sodium chloride solution=6:4) $C_{25}H_{28}N_4O_3 \times HCl$ (432.54/468.99) Mass spectrum: $(M+H)^+=433$ $(M-H)^-=431$ $(M+Cl)^-=467/69$ (chlorine isotope)

EXAMPLE 37

3-{N-benzyl-3-[3-methyl-4-(2,5-dihydropyrrol-1-yl-carbonyl)-phenyl]-propargylamino}-benzamidine-hydrochloride

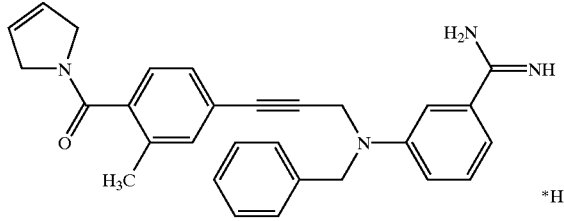

Prepared analogously to Example 1e from 3-{N-benzyl-3-[3-methyl-4-(2,5-dihydropyrrol-1-yl-carbonyl)-phenyl]-propargylamino}-benzonitrile, ethanol saturated with hydrogen chloride gas and ammonium carbonate.

Yield: 13% of theory $R_f$ value: 0.38 (silica gel; dichloromethane/ethanol=3:1) $C_{29}H_{28}N_4O\times HCl$ (448.58/485.04) Mass spectrum: $(M+H)^+$=449 $(M+Cl)^-$=483/85 (chlorine isotope)

EXAMPLE 38

3-[N-benzyl-3-(4-isobutyryl-3-methyl-phenyl)-propargylamino]-benzamidine-hydrochloride

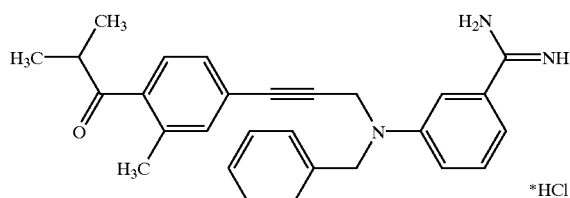

Prepared analogously to Example 1e from 3-[N-benzyl-3-(4-isobutyryl-3-methyl-phenyl)-propargylamino]-benzonitrile, ethanol saturated with hydrogen chloride gas and ammonium carbonate.

Yield: 77% of theory $R_f$ value: 0.44 (silica gel; dichloromethane/ethanol=3:1) $C_{28}H_{29}N_3O\times HCl$ (423.57/460.03) Mass spectrum: $(M+H)^+$=424 $(M+Cl)^-$=458/60 (chlorine isotope)

EXAMPLE 39

3-[N-benzyl-3-(4-benzoyl-3-methyl-phenyl)-propargylamino]-benzamidine-hydrochloride

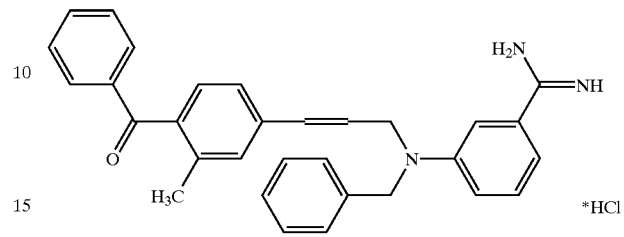

Prepared analogously to Example 1e from 3-[N-benzyl-3-(4-benzoyl-3-methyl-phenyl)-propargylamino]-benzonitrile, ethanol saturated with hydrogen chloride gas and ammonium carbonate.

Yield: 75% of theory $R_f$ value: 0.47 (silica gel; dichloromethane/ethanol=3:1) $C_{31}H_{27}N_3O\times HCl$ (457.59/494.05) Mass spectrum: $(M+H)^+$=458 $(M+Cl)^-$=492/94 (chlorine isotope)

EXAMPLE 40

3-{N-benzyl-3-[2'-aminosulphonyl-biphenyl-4-yl]-propargylamino}-benzamidine-hydrochloride

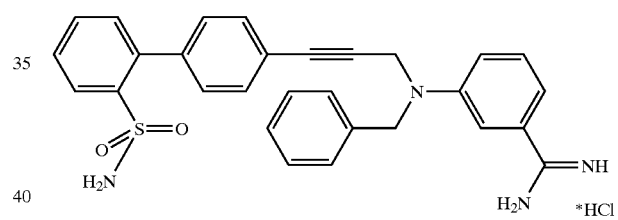

Prepared analogously to Example 1e from 3-{N-benzyl-3-[2'-tert.butylaminosulphonyl-biphenyl-4-yl]-propargylamino}-benzonitrile, ethanol saturated with hydrogen chloride gas and ammonium carbonate.

Yield: 10% of theory $R_f$ value: 0.45 (silica gel; dichloromethane/ethanol=3:1) $C_{29}H_{26}N_4O_2S\times HCl$ (494.62/531.08) Mass spectrum: $(M+H)^+$=495 $(M-H)^-$=493 $(M+Cl)^-$=529/31 (chlorine isotope)

EXAMPLE 41

3-{N-benzyl-3-[2'-aminosulphonyl-biphenyl-4-yl]-propylamino}-benzamidine-hydrochloride

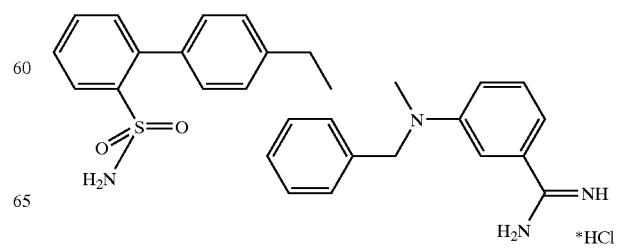

Prepared analogously to Example 7 from 3-{N-benzyl-3-[2'-aminosulphonyl-biphenyl-4-yl]-propargylamino}-benzamidine-hydrochloride, palladium on activated charcoal (10%) and hydrogen in ethanol.

Yield: 100% of theory $R_f$ value: 0.18 (Reversed phase RP 8; methanol/5% sodium chloride solution=6:4) $C_{29}H_{30}N_4O_2S \times HCl$ (498.65/535.11) Mass spectrum: $(M+H)^+=499$ $(M+Cl)^-=533/35$ (chlorine isotope)

EXAMPLE 42

3-{N-(pyridin-2-ylmethyl)-3-[3-methyl-4-(pyrrolidin-1-yl-carbonyl)-phenyl]-propargyl-amino}-benzamidine-dihydrochloride

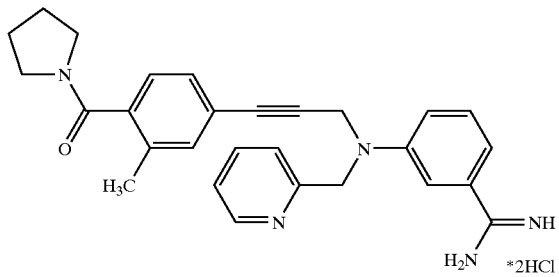

Prepared analogously to Example 1e from 3-{N-(pyridin-2-ylmethyl)-3-[3-methyl-4-(pyrrolidin-1-yl-carbonyl)-phenyl]-propargylamino}-benzonitrile, ethanol saturated with hydrogen chloride gas and ammonium carbonate.

Yield: 20% of theory $R_f$ value: 0.15 (silica gel; dichloromethane/ethanol=95:5) $C_{28}H_{29}N_5O \times 2$ HCl (451.57/524.49) Mass spectrum: $(M+H)^+=452$

EXAMPLE 43

3-{N-(pyridin-3-ylmethyl)-3-[3-methyl-4-(pyrrolidin-1-yl-carbonyl)-phenyl]-propargyl-amino}-benzamidine-dihydrochloride

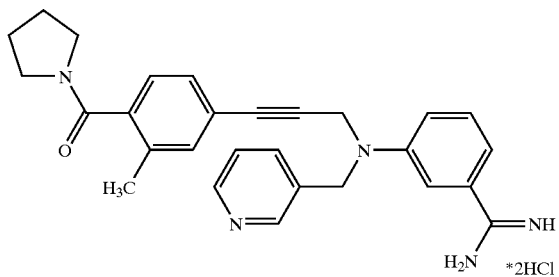

Prepared analogously to Example 1e from 3-{N-(pyridin-3-ylmethyl)-3-[3-methyl-4-(pyrrolidin-1-yl-carbonyl)-phenyl]-propargylamino}-benzonitrile, ethanol saturated with hydrogen chloride gas and ammonium carbonate.

Yield: 25% of theory $R_f$ value: 0.13 (silica gel; dichloromethane/ethanol=95:5) $C_{28}H_{29}N_5O \times 2$ HCl (451.57/524.49) Mass spectrum: $(M+H)^+=452$ $(M+Cl)^-=486/88$ (chlorine isotope)

EXAMPLE 44

3-[N-(2-ethoxycarbonylethyl)-3-(4-cyclopentylcarbonyl-3-methylphenyl)-propargylamino]-benzamidine-hydrochloride

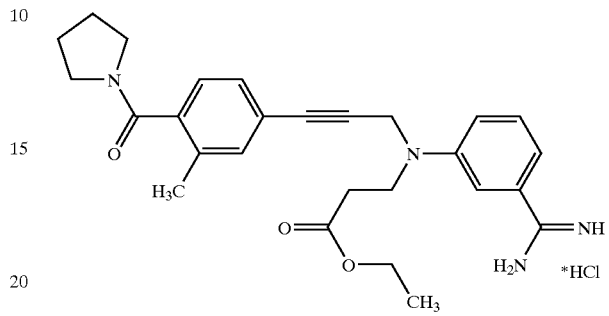

Prepared analogously to Example 1e from 3-[N-(2-ethoxycarbonylethyl)-3-(4-cyclopentyl-carbonyl-3-methylphenyl)-propargylamino]-benzonitrile, ethanol saturated with hydrogen chloride gas and ammonium carbonate.

Yield: 18% of theory $R_f$ value: 0.19 (silica gel; dichloromethane/ethanol=4:1) $C_{28}H_{33}N_3O_3 \times HCl$ (459.59/496.05) Mass spectrum: $(M+H)^+=460$ $(M+Cl)^-=494/96$ (chlorine isotope)

EXAMPLE 45

3-[N-(4-ethoxycarbonylphenylmethyl)-3-(2'-aminosulphonylbiphenyl-4-yl)-propargyl-amino]-benzamidine-hydrochloride

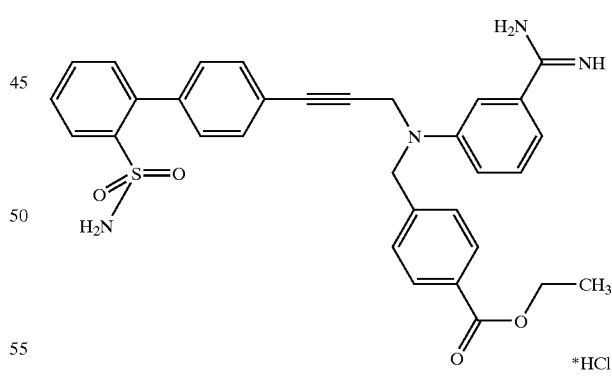

Prepared analogously to Example 1e from 3-[N-(4-ethoxycarbonylphenylmethyl)-3-(2'-tert.butylaminosulphonylbiphenyl-4-yl)-propargylamino]-benzonitrile, ethanol saturated with hydrogen chloride gas and ammonium carbonate.

Yield: 26% of theory $R_f$ value: 0.18 (silica gel; dichloromethane/ethanol=4:1) $C_{32}H_{30}N_4O_4S \times HCl$ (566.69/603.145) Mass spectrum: $(M+H)^+=567$ $(M-H)^-=565$ $(M+Cl)^-=601/03$ (chlorine isotope)

EXAMPLE 46

Dry ampoule containing 75 mg of active substance per 10 ml

Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

EXAMPLE 47

Dry ampoule containing 35 mg of active substance per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

EXAMPLE 48

Tablet containing 50 mg of active substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 49

Tablet containing 350 mg of active substance

Composition:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 50

Capsules containing 50 mg of active substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 51

Capsules containing 350 mg of active substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 52

Suppositories containing 100 mg of active substance 1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. This is then cooled to 38° C. and poured into slightly chilled suppository moulds.

What is claimed is:

1. A compound of the formula (I)

$$Ar-A-(CH_2)_{\overline{n}}-(CHR_1)-X \underset{Y_1}{\overset{Y_2=Y_3}{\diagup}} \underset{R_5}{\overset{Y_4,}{\diagdown}} \quad (I)$$

wherein

A is an ethynylene or an ethylene group, n is 0 or 1, $R_1$ is a hydrogen atom, a $C_{1-3}$-alkyl, carboxy-$C_{1-3}$-alkyl, phenyl, phenyl-$C_{1-3}$-alkyl, N-$C_{1-3}$-alkylaminocarbonyl-$C_{1-3}$-alkyl, N,N-Di-($C_{1-3}$-alkyl)-aminocarbonyl-$C_{1-3}$-alkyl or $C_{4-7}$-cycloalkyleneimino-carbonyl-$C_{1-3}$-alkyl group, Ar is a phenyl group substituted by the groups $R_2$ to $R_4$, where $R_2$ is a carbonyl group which is substituted by a $C_{3-7}$-cycloalkylamino group which may additionally be substituted in each case at the amino-nitrogen atom by a $C_{1-5}$-alkyl, $C_{3-7}$-cycloalkyl, carboxy-$C_{1-3}$-alkyl, amino-$C_{1-4}$-alkyl, $C_{1-3}$-amino-$C_{1-4}$-alkyl, 2-[di-($C_{1-3}$-alkyl)-amino]-ethyl, 3-[di-($C_{1-3}$-alkyl)-amino]-propyl, phenyl, pyridyl, pyrrolidinyl, piperidinyl, 2,5-dihydro-1H-pyrrolyl or 1,2,5,6-tetrahydropyridinyl group, by a pyrrolyl group, optionally substituted by one or two $C_{1-3}$-alkyl groups, or by a $C_{3-6}$-cycloalkyleneimino or $C_{3-6}$-cycloalkenyleneimino group optionally substituted by a $C_{1-3}$-alkyl, carboxy-$C_{1-3}$-alkyl, hydroxy, hydroxy-$C_{1-3}$-alkyl, amino, carboxy, carboxy-$C_{1-3}$-alkoxy-$C_{1-3}$-alkyl, carboxy-$C_{1-3}$-alkylamino-$C_{1-3}$-alkyl or carboxy-$C_{1-3}$-alkylaminocarbonyl-$C_{1-3}$-alkyl group, with the proviso that the hydroxy and the amino groups are not bound in the 2-position;

$R_3$ is a hydrogen, fluorine, chlorine, bromine or iodine atom, a formyl or trifluoromethyl group, a $C_{1-3}$-alkoxy, amino, $C_{1-2}$-alkylamino, di-($C_{1-2}$-alkyl)-amino or $C_{1-2}$-alkanoylamino group, a $C_{1-4}$-alkyl, $C_{2-4}$-alkenyl, $C_{2-4}$-Alkynyl or $C_{3-4}$-cycloalkyl group optionally substituted by a hydroxy, $C_{1-3}$-alkoxy, carboxy, carboxy-$C_{1-3}$-alkoxy or carboxy-$C_{1-3}$-alkylaminocarbonyl group; and $R_4$ is a hydrogen, fluorine, chlorine, bromine or iodine atom, a $C_{1-3}$-alkyl, trifluoromethyl or $C_{1-3}$-alkoxy group, X is an oxygen or sulphur atom, a methylene group optionally substituted by one or two $C_{1-3}$-alkyl groups, a carbonyl, sulphinyl, sulphonyl, imino or N-($C_{1-3}$-alkyl)-imino group, a N-(phenyl-$C_{1-3}$-alkyl)-imino or N-(pyridyl-$C_{1-3}$-alkyl)-imino group optionally substituted by a carboxy group, a N-($C_{1-3}$-alkyl)-carbonylimino, N-(carboxy-$C_{1-3}$-alkyl)-imino, $C_{1-3}$-alkylaminocarbonyl-$C_{1-3}$-alkylimino, di-($C_{1-3}$-alkyl)-aminocarbonyl or $C_{1-3}$-alkylimino group, $R_5$ is a cyano or $C_{1-2}$-alkyl-cyano group or an amidino group and $Y_1$ is the group $CR^w$, $Y_2$ is the group $CR^x$, $Y_3$ is the group $CR^y$ and $Y_4$ is the group $CR^z$ or one or two of the groups $Y_1$ to $Y_4$ is a nitrogen atom and in each case the remainder of the groups $Y_1$ to $Y_4$ are three or two of the groups $CR^w$ to $CR^z$, where $R^w$, $R^x$, $R^y$ and $R^z$ in each case are hydrogen or one or two of the groups $R^w$ to $R^z$ independently of one another in each case are fluorine, chlorine or bromine, a straight-chain $C_{1-3}$-alkyl group, a hydroxy, $C_{1-3}$-alkoxy, amino, $C_{1-3}$-alkylamino or di-($C_{1-3}$-alkyl)-amino group and the remainder of the groups $R^w$ to $R^z$ in each case are hydrogen, where the hydrogen atoms in the methyl and methoxy groups mentioned in the definition of the above groups or in the methyl moieties contained in the groups of formula I defined hereinbefore may be wholly or partially replaced by fluorine atoms, or a tautomer, stereoisomer, or salt thereof.

2. A compound of the formula I according to claim 1, wherein

A is an ethynylene group, or a tautomer, stereoisomer, or salt thereof.

3. A compound of the formula I according to claim 1, wherein

A is an ethynylene or an ethylene group, n is 0 or 1, $R_1$ is a hydrogen atom, a $C_{1-3}$-alkyl, phenyl or carboxy-$C_{1-3}$-alkyl group, Ar is a phenyl group substituted by the groups $R_2$ to $R_4$, where $R_2$ is a carbonyl group which is substituted by a $C_{3-7}$-cycloalkylamino group which may additionally be substituted in each case at the amino-nitrogen atom by a $C_{1-5}$-alkyl group, or by a $C_{3-6}$-cycloalkyleneimino or $C_{3-6}$-cycloalkenyleneimino group optionally substituted by a $C_{1-3}$-alkyl, carboxy-$C_{1-3}$-alkyl, hydroxy, hydroxy-$C_{1-3}$-alkyl, amino or carboxy group, with the proviso that the hydroxy and the amino groups are not bound in the 2-position;

$R_3$ is a hydrogen, fluorine, chlorine or bromine atom or a trifluoromethyl group, a $C_{1-3}$-alkoxy, amino, $C_{1-2}$-alkylamino, di-($C_{1-2}$-alkyl)-amino or $C_{1-2}$-alkanoylamino group, a $C_{1-4}$-alkyl, $C_{2-4}$-alkynyl or $C_{3-4}$-cycloalkyl group; and $R_4$ is a hydrogen atom or a $C_{1-3}$-alkyl group, X is an oxygen atom, an imino, N-($C_{1-3}$-alkyl)-imino group, a N-benzyl-imino or N-(pyridyl-$C_{1-3}$-alkyl)-imino group optionally substituted by a carboxy group, a N-($C_{1-3}$-alkyl)-carbonylimino or N-(carboxy-$C_{1-3}$-alkyl)-imino group, $R_5$ is a cyano group or an aminomethyl or amidino and $Y_1$ is the group $CR^w$, $Y_2$ is the group $CR^x$, $Y_3$ is the group $CR^y$ and $Y_4$ is the group $CR^z$ or one of the groups $Y_1$ to $Y_4$ is a nitrogen atom and the remainder of the groups $Y_1$ to $Y_4$ represent three of the groups $CR^w$ to $CR^z$, where $R^w$, $R^x$, $R^y$ and $R^z$ in each case are a hydrogen atom or one of the groups $R^w$ to $R^z$ is a chlorine atom, a $C_{1-3}$-alkyl group, a hydroxy, $C_{1-3}$-alkoxy, amino or $C_{1-3}$-alkylamino group and the remainder of the groups $R^w$ to $R^z$ in each case represent a hydrogen atom, while the hydrogen atoms in the methyl and methoxy groups mentioned in the definition of the above groups or in the methyl moieties contained in the groups of formula I defined above may be wholly or partially replaced by fluorine atoms, or a tautomer, stereoisomer, or salt thereof.

4. A compound of the formula I according to claim 3, wherein

A is an ethynylene group, or a tautomer, stereoisomer, or salt thereof.

5. A compound of formula

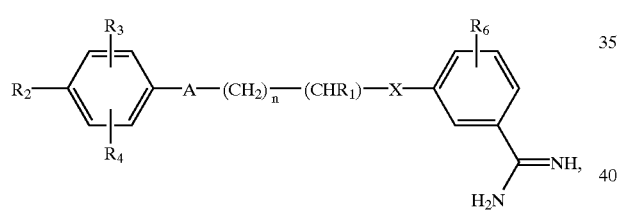

(Ia)

wherein

A is an ethylene or ethynylene group, n is 0 or 1, $R_1$ is a hydrogen atom, a $C_{1-3}$-alkyl, phenyl or carboxy-$C_{1-3}$-alkyl group, $R_2$ is a carbonyl group which is substituted
  by a $C_{3-7}$-cycloalkylamino group which may additionally be substituted in each case at the amino-nitrogen atom by a $C_{1-5}$-alkyl group, or
  by a pyrrolidino or 2,5-dihydro-1H-pyrrolyl group optionally substituted by a $C_{1-3}$-alkyl, carboxy-$C_{1-3}$-alkyl, hydroxy, hydroxy-$C_{1-3}$-alkyl, amino or carboxy group, with the proviso that the hydroxy and amino groups are not bound in the 2-position, $R_3$ is a hydrogen, fluorine, chlorine or bromine atom or a trifluoromethyl group, a $C_{1-3}$-alkoxy or a $C_{1-4}$-alkyl group and $R_4$ is a hydrogen atom or a $C_{1-3}$-alkyl group, X is an oxygen atom, an imino, N-($C_{1-3}$-alkyl)-imino, N-benzyl-imino, N-($C_{1-3}$-alkyl)-carbonylimino or N-(carboxy-$C_{1-3}$-alkyl)-imino group, $R_6$ is a chlorine atom or a $C_{1-3}$-alkyl, hydroxy, $C_{1-3}$-alkoxy, amino or $C_{1-3}$-alkylamino group, while the hydrogen atoms in the methyl and methoxy groups mentioned in the definition of the above groups or in the methyl moieties contained in the groups of formula Ia defined above may be wholly or partially replaced by fluorine atoms, or a tautomer, stereoisomer, or salt thereof.

6. A compound of the formula I according to claim 5, wherein

A is an ethynylene group, or a tautomer, stereoisomer, or salt thereof.

7. A compound selected from the group consisting of:
(1) 4-hydroxy-3-{3-[4-(pyrrolidin-1-yl-carbonyl)-3-methyl-phenyl]-propargylamino}-benzamidine,
(2)
(3) 3-{N-methyl-3-[3-methyl-4-(pyrrolidin-1-yl-carbonyl)-phenyl]-propargylamino}-benzamidine,
(4) 3-{N-acetyl-3-[3-methyl-4-(pyrrolidin-1-yl-carbonyl)-phenyl]-propargylamino }-benzamidine,
(5) 3-{4-[3-methyl-4-(pyrrolidin-1-yl-carbonyl)-phenyl]-but-3-inylamino}-benzamidine,
(6) 3-{3-[3-methyl-4-(pyrrolidin-1-yl-carbonyl)-phenyl]-propyl-amino}-benzamidine,
(7) 3-{3-[2,5-dimethyl-4-(pyrrolidin-1-yl-carbonyl)-phenyl]-propargylamino}-benzamidine,
(8) 3-{3-[3-methyl-4-(pyrrolidin-1-yl-carbonyl)-phenyl]-propargyl-oxy}-benzamidine,
(9) 3-{1-methyl-3-[3-methyl-4-(pyrrolidin-1-yl-carbonyl)-phenyl]-propargylamino}-benzamidine,
(10) 3-{N-hydroxycarbonylmethyl-3-[3-methyl-4-(pyrrolidin-1-yl-carbonyl)-phenyl]-propargylamino}-benzamidine,
(11) 3-{3-[4-(pyrrolidin-1-yl-carbonyl)-phenyl]-propargylamino}-benzamidine,
(12) 3-{N-methyl-3-[3-methyl-4-(pyrrolidin-1-yl-carbonyl)-phenyl]-propylamino}-benzamidine,
(13) 3-{N-methyl-3-[3-methyl-4-(2,5-dihydropyrrol-1-yl-carbonyl)-phenyl]-propargylamino}-benzamidine,
(14) 3-{3-[3-methyl-4-(2,5-dihydropyrrol-1-yl-carbonyl)-phenyl]-propargylamino}-benzamidine,
(15) 3-{N-benzyl-3-[3-methyl-4-(pyrrolidin-1-yl-carbonyl)-phenyl]-propargylamino}-benzamidine,
(16) 3-{N-(4-hydroxycarbonylphenylmethyl)-3-[3-methyl-4-(pyrrolidin-1-yl-carbonyl)-phenyl]-propargylamino}-benzamidine,
(17) 3-{N-(3-hydroxycarbonylphenylmethyl)-3-[3-methyl-4-(pyrrolidin-1-yl-carbonyl)-phenyl]-propargylamino}-benzamidine,
(18) 3-{N-(2-hydroxycarbonylethyl)-3-[3-methyl-4-(pyrrolidin-1-yl-carbonyl)-phenyl]-propargylamino}-benzamidine,
(19) 3-{N-benzyl-3-[3-methyl-4-(2,5-dihydropyrrol-1-yl-carbonyl)-phenyl]-propargylamino}-benzamidine,
(20) 3-{N-(pyridin-3-ylmethyl)-3-[3-methyl-4-(pyrrolidin-1-yl-carbonyl)-phenyl]-propargylamino}-benzamidine, and
(21) 3-[N-(2-ethoxycarbonylethyl)-3-(4-cyclopentylcarbonyl-3-methylphenyl)-propargylamino]-benzamidine
or
or a salt thereof.

8. A compound of the formula I according to claim 1, wherein $R_5$ does not contain a cyano group.

9. A pharmaceutical composition comprising a compound according to claim 8, together with one or more inert carriers or diluents.

* * * * *